United States Patent
Morita et al.

(10) Patent No.: US 6,500,439 B1
(45) Date of Patent: Dec. 31, 2002

(54) COPOLYMER FOR COSMETICS

(75) Inventors: Masamichi Morita, Settsu (JP); Motonobu Kubo, Settsu (JP)

(73) Assignee: Daikin Industries, Ltd., Osaka (JP)

( * ) Notice: Subject to any disclaimer, the term of this patent is extended or adjusted under 35 U.S.C. 154(b) by 0 days.

(21) Appl. No.: 09/445,243

(22) PCT Filed: May 25, 1998

(86) PCT No.: PCT/JP98/02268

§ 371 (c)(1),
(2), (4) Date: Dec. 3, 1999

(87) PCT Pub. No.: WO98/55078

PCT Pub. Date: Dec. 10, 1998

(30) Foreign Application Priority Data

Jun. 4, 1997 (JP) ............................................. 9-146284
Jul. 9, 1997 (JP) ............................................. 9-183529

(51) Int. Cl.[7] .............................. A61K 6/00; A61K 7/06
(52) U.S. Cl. ...................................... 424/401; 424/70.1
(58) Field of Search .............................. 424/401, 70.1; 524/504; 106/285

(56) References Cited

U.S. PATENT DOCUMENTS

| | | | |
|---|---|---|---|
| 4,059,688 A | * 11/1977 | Rosenberg et al. | 424/71 |
| 4,803,067 A | 2/1989 | Brunetta et al. | |
| 4,808,651 A | * 2/1989 | Blickle et al. | 524/366 |
| 5,112,917 A | * 5/1992 | Cohen | 525/185 |
| 5,164,426 A | * 11/1992 | Shimizu et al. | 523/201 |
| 5,304,334 A | 4/1994 | Lahanas et al. | |
| 5,330,681 A | 7/1994 | Brunetta et al. | |
| 5,571,858 A | 11/1996 | de La Poterie et al. | |
| 5,578,311 A | 11/1996 | Nagatania et al. | |
| 5,614,123 A | * 3/1997 | Kubo et al. | 252/862 |
| 5,637,142 A | * 6/1997 | Kubo et al. | 106/285 |
| 5,639,820 A | * 6/1997 | Kubo et al. | 524/758 |
| 5,660,888 A | * 8/1997 | Grenfell et al. | 427/385.5 |
| 5,667,772 A | 9/1997 | Zastrow et al. | |
| 5,750,797 A | * 5/1998 | Vitcak et al. | 568/683 |
| 5,851,539 A | 12/1998 | Mellul et al. | |
| 5,883,175 A | * 3/1999 | Kubo et al. | 524/458 |
| 5,925,611 A | 7/1999 | Flynn et al. | |
| 5,945,108 A | * 8/1999 | Sugawara et al. | 424/401 |
| 5,965,659 A | * 10/1999 | Kubo et al. | 524/504 |
| 6,002,048 A | 12/1999 | Fujii et al. | |
| 6,060,626 A | 5/2000 | Fujii et al. | |
| 6,136,331 A | * 10/2000 | Morita et al. | 424/401 |

FOREIGN PATENT DOCUMENTS

| | | | | |
|---|---|---|---|---|
| EP | 0079590 | | 5/1983 | |
| EP | 0206671 | | 12/1986 | |
| EP | 0263514 | | 4/1988 | |
| EP | 0388582 | | 9/1990 | |
| EP | 0412771 | | 2/1991 | |
| EP | 0682146 | | 11/1995 | |
| JP | 58-83011 A | | 5/1983 | |
| JP | 62-123107 | | 6/1987 | |
| JP | 62-223105 | | 10/1987 | |
| JP | 62-249913 | | 10/1987 | |
| JP | 63-2916 | | 1/1988 | |
| JP | 63-95207 A | | 4/1988 | |
| JP | 2247110 | | 10/1990 | |
| JP | 3-76713 A | | 4/1991 | |
| JP | 3046444 | | 7/1991 | |
| JP | 5-117333 A | | 5/1993 | |
| JP | 6-25361 A | | 2/1994 | |
| JP | WO94/11456 | * | 5/1994 | C09K/3/18 |
| JP | 6-227942 | | 8/1994 | |
| JP | 6-228534 A | | 8/1994 | |
| JP | 9-012428 A | | 1/1997 | |
| JP | WO98/01104 | * | 1/1998 | A61K/7/00 |
| WO | WO 95/18194 | * | 6/1995 | |
| WO | 96/22356 | | 7/1996 | |

OTHER PUBLICATIONS

"Precision & Electronics Cleaning" [online]. 3M Corporation, 1996 [retrieved on May 22, 1997]. Retrieved from the Internet: <URL:www.mmm.com/market/industrial/fluids/preclean.html>.*

Jun. 1996 HFE–7100 Product Information Sheet, 3M Specialty Chemicals Division, St. Paul, MN.

Owens et al., "Performance of Hydrofluoroethers in Cleaning Applications," Presented Oct. 1995, International CFC and Halon Alternatives Conference, Washington, D.C.

Pantini et al., "Perfluoropolyethers Status and New Developments," Cosmetics & Toiletries, pp. 71–80, vol. 106 (Oct. 1991).

Seikya et al., "A continuing search for new refrigerants," Chemtech, pp. 44–48 (Dec. 1996).

* cited by examiner

Primary Examiner—Michael G. Hartley
Assistant Examiner—Michael A. Willis
(74) Attorney, Agent, or Firm—Birch, Stewart, Kolasch & Birch, LLP

(57) ABSTRACT

A copolymer for cosmetics, which is obtained by polymerizing (A) 5 to 95% by weight of a fluorine-containing (meth)acrylate, and (B) 5 to 95% by weight of at least one fluorine-free monomer selected from the group consisting of (i) a silicone macromonomer, (ii) a polyalkylene glycol (meth)acrylate, (iii) an alkyl (meth)acrylate, and (iv) an alkyl (meth)acrylate macromonomer, can be easily incorporated in cosmetics and can form a film excellent in water resistance, water- and oil-repellency, feeling when used, and safety. This copolymer for cosmetics can improve the drawbacks of powder treated with a fluorine-containing compound.

14 Claims, No Drawings

COPOLYMER FOR COSMETICS

This application is the national phase under 35 U.S.C. §371 of PCT International Application No. PCT/JP98/02268 which has an International filing date of May 25, 1998, which designated the United States of America.

FIELD OF THE INVENTION

The present invention relates to a copolymer for cosmetics, which copolymer can be easily incorporated in cosmetics and is excellent in water resistance, water- and oil-repellency, feeling when used, and safety, and also to a cosmetic containing said copolymer. The copolymer for cosmetics acts as a film forming agent for cosmetics, a compatibilizer or an emulsifier between a fluorine-containing raw material and a fluorine-free raw material, and a surface treatment agent for fluorine-containing compound-treated powder and silicone-treated powder.

DESCRIPTION OF RELATED ART

Heretofore, a hydrocarbon-based emulsion resin has been generally used as a film forming agent for cosmetics. The purpose of incorporating the film forming agent is to form a film after the application of a cosmetic so that the pigment and other effective ingredients are held on the skin for a long period of time. However, the water resistance and water- and oil-repellency of the conventional film forming agents are so insufficient that the film is destroyed by water coming into contact the film or by sweat or skin fat secreted from the skin. Recently, an acryl-silicone copolymer is used as a copolymer which overcame the drawback, i.e., insufficient water resistance and water-repellency, of the hydrocarbon-based emulsion resin (Japanese Patent Kokai Publication (JP-A) No. 247,110/1990). The acryl-silicone copolymer is a copolymer comprising a hydrocarbon-based acrylate and a silicone macromonomer and the film thereof has excellent water resistance and water-repellency.

However, since the acryl-silicone copolymer also has almost no water-repellency, a messy makeup caused by skin fat cannot be prevented. There has been known a technology in which a copolymer between an alkyl (meth)acrylate having a long-chain alkyl group of 8 or more carbon atoms and a polyfluoroalkyl (meth)acrylate having an polyfluoroalkyl group of 4 or more carbon atoms is contained as a film forming agent so as to impart oil repellency (Japanese Patent Kokoku Publication (JP-B) No. 46,444/1991). This copolymer is associated with a drawback that no film is formed from an emulsion containing the copolymer dispersed in water because the softening point of the copolymer is higher than skin temperature. On the other hand, if the molecular weight of the copolymer is lowered to a point which makes the copolymer soluble in a solvent so that a film can be formed from the solution, the copolymer does not exhibit oil repellency.

Meanwhile, as a recent trend, a fluorine-containing raw material, such as fluorine-containing compound-treated powder and perfluoropolyether, is incorporated into cosmetics. Since the affinity of these fluorine-containing raw materials for a conventionally employed fluorine-free raw material such as a hydrocarbon-based raw material or a silicone-based raw material is so poor that it is very difficult to incorporate the above-described fluorine-containing raw material in a cosmetic in a stable manner. Therefore, there is a need for the development of a compatibilizer capable of enhancing the affinity between the fluorine-containing raw material and the fluorine-free raw material.

SUMMARY OF THE INVENTION

After extensive studies to overcome the foregoing problems, the present inventors have found that a copolymer, which is a fluorine-containing (meth)acrylate copolymer having specific ingredients and soluble or dispersible in water or a solvent, has excellent characteristics as a copolymer for cosmetics. More specifically, the copolymer for cosmetics can be easily incorporated in conventional cosmetics and, when applied to a skin, the cosmetic incorporated with the copolymer forms a film excellent in water resistance, water- and oil-repellency, feeling when used, and safety.

Further, the copolymer for cosmetics acts as a compatibilizer between a fluorine-containing raw material and a fluorine-free raw material. In this way, the copolymer is effective in stabilizing the cosmetics.

The present invention provides a copolymer for cosmetics, said copolymer comprising (A) 5 to 95% by weight of the repeating units derived from a fluorine-containing (meth)acrylate, and (B) 95 to 5% by weight of the repeating units derived from at least one fluorine-free monomer selected from the group consisting of a silicone macromonomer, a polyalkylene glycol (meth)acrylate, an alkyl (meth)acrylate macromonomer, and an alkyl (meth)acrylate, wherein the copolymer comprises:

(i) a fluorine-containing (meth)acrylate and a silicone macromonomer, (ii) a fluorine-containing (meth)acrylate and a polyalkylene glycol (meth)acrylate, (iii) a fluorine-containing (meth)acrylate and an alkyl (meth)acrylate macromonomer, (iv) a fluorine-containing (meth)acrylate and a $C_{1-4}$ alkyl-containing alkyl (meth)acrylate, (v) a fluorine-containing (meth)acrylate, a silicone macromonomer, and a $C_{1-22}$ alkyl-containing alkyl (meth)acrylate, or (vi) a fluorine-containing (meth)acrylate, a silicone macromonomer, and an alkyl (meth)acrylate macromonomer.

The fluorine-containing (meth)acrylate to be used in the copolymer for cosmetics may have the following structural formula:

(I-1)

wherein Rf is a polyfluoroalkyl group having 6 to 16 carbon atoms or a perfluoropolyether group; and A is an alkylene group having 1 to 4 carbon atoms,

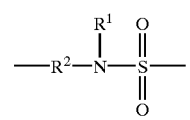

(wherein $R^1$ is an alkyl group having 1 to 4 carbon atoms and $R^2$ is an alkylene group having 1 to 4 carbon atoms), or

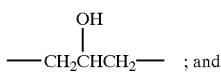
;and

X is a hydrogen atom or a methyl group.

Further, the fluorine-containing (meth)acrylate may be, for example, a fluorine-containing (meth)acrylate macromonomer having the following structural formula:

(I-2)

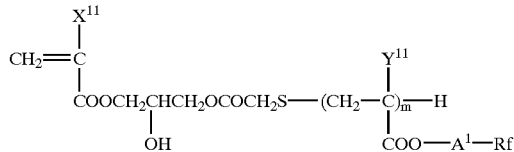

wherein Rf is a polyfluoroalkyl group having 6 to 16 carbon atoms or a perfluoropolyether group; $A^1$ is an alkylene group having 1 to 4 carbon atoms,

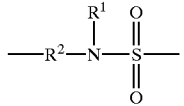

(wherein $R^1$ is an alkyl group having 1 to 4 carbon atoms and $R^2$ is an alkylene group having 1 to 4 carbon atoms), or

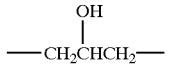

$X^{11}$ is a hydrogen atom or a methyl group; $Y^{11}$ is a hydrogen atom or a methyl group; and m is 5 to 100.

Specific examples of the perfluoropolyether group include the following.

$F(CF(CF_3)CF_2O)_nCF_2CF_2$— (wherein n is an integer of 3 to 30), $CF_3O(CF(CF_3)CF_2O)_n(CF_2O)_mCF_2$— (wherein n is an integer of 2 to 30 and m is an integer of 3 to 70), $CF_3O(CF_2CF_2O)_n(CF_2O)_mCF_2$— (wherein n is an integer of 2 to 40 and m is an integer of 4 to 70), and $F(CF_2CF_2CF_2O)_nCF_2CF_2$— (wherein n is an integer of 3 to 30).

It is preferable that the number average molecular weight (as measured by $^{19}$F-NMR) of the perfluoropolyether group is in the range of from 500 to 5,000.

Specific examples of the fluorine-containing (meth) acrylate include the following.

$CF_3(CF_2)_7(CH_2)OCOCH=CH_2$, $CF_3(CF_2)_6(CH_2)OCOC(CH_3)=CH_2$, $(CF_3)_2CF(CF_2)_6(CH_2)_2OCOCH=CH_2$, $CF_3(CF_2)_7(CH_2)_2OCOC(CH_3)=CH_2$, $CF_3(CF_2)_7(CH_2)_2OCOCH=CH_2$, $HCF_2(CF_2)_7(CH_2)_2OCOCH=CH_2$, $CF_3(CF_2)_5(CH_2)_2OCOCH=CH_2$, $CF_3(CF_2)_7SO_2N(CH_3)(CH)_2OCOCH=CH_2$, $CF_3(CF_2)_7SO_2N(C_2H_5)(CH_2)_2OCOC(CH_3)=CH_2$, $(CF_3)_2CF(CF_2)_6CH_2CH(OCOCH_3)CH_2OCOC(CH_3)=CH_2$, $(CF_3)_2CF(CF_2)_6CH_2CH(OH)CH_2OCOCH=CH_2$,

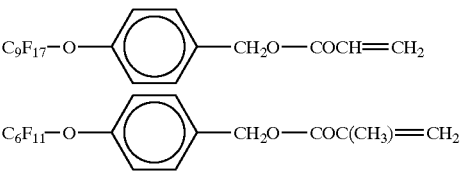

$F(CF(CF_3)CF_2O)_{10}CF_2CF_2$—$COOCH_2CH_2CH=CH_2$,

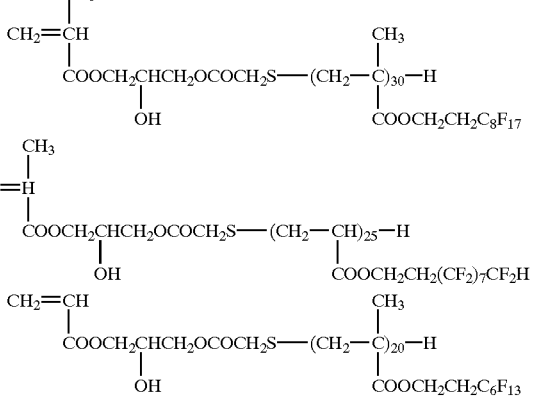

These fluorine-containing (meth)acrylates may be used in a combination of two or more of them.

In the present invention, the fluorine-free monomer which is used in the radical polymerization with the fluorine-containing (meth)acrylate is classified into four types, namely, a silicone macromonomer, a polyalkylene glycol (meth)acrylate, an alkyl (meth)acrylate macromonomer, and an alkyl (meth)acrylate.

The silicone macromonomer has a structural formula such as the following formula:

(II-1)

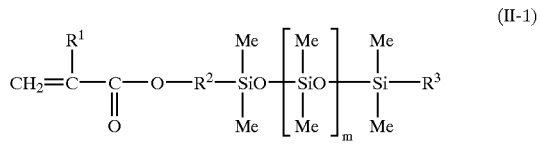

wherein Me is a methyl group and $R^1$ is a methyl group or a hydrogen atom; $R^2$ is a divalent saturated hydrocarbon group having 1 to 10 carbon atoms which has a straight or branched carbon chain and which may be disjoined by one or two ether linkages in some cases; $R^3$ is an alkyl group having 1 to 4 carbon atoms; and m is 3 to 300.

Specific examples of $R^2$ include the following:

—$CH_2$—, —$(CH_2)_3$—, —$(CH_2)_6$—, —$(CH_2)_{10}$—, —$CH_2$—$CH(CH_3)$—$(CH_2)$—, —$CH_2$—$CH_2OCH_2CH_2CH_2$—,

—$CH_2CH_2OCH_2CH(CH_3)CH_2$—, and —$CH_2CH_2OCH_2CH_2OCH_2CH_2CH_2$—.

The silicone macromonomer is advantageously used as a dimethylpolysiloxane compound having at one end of the molecular chain thereof a radically polymerizable group. Specific examples of the silicone macromonomer include the following:

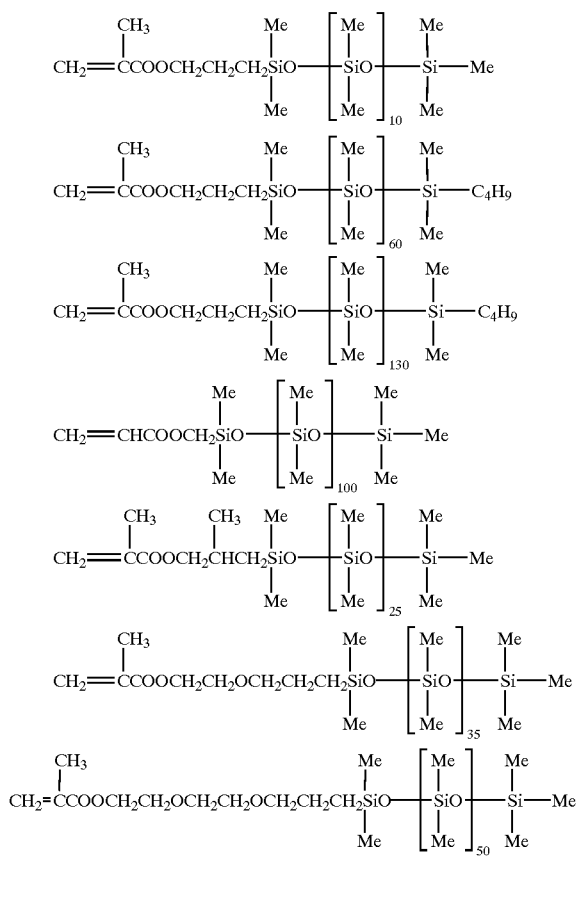

wherein Me is a methyl group.

The polyalkylene glycol (meth)acrylate has the following formula:

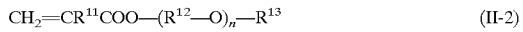

wherein $R^{11}$ and $R^{13}$ are each a hydrogen atom or a methyl group; $R^{12}$ is an alkylene group having 2 to 6 carbon atoms; and n is an integer 1 to 50.

Specific examples of the polyalkylene glycol (meth)acrylate include 2-hydroxyethyl (meth)acrylate, and $CH_2=C(CH_3)COO(CH_2CH_2O)_nH$ (wherein n is 2, 5, or 8).

The alkyl (meth)acrylate macromonomer has, for example, the following structural formula:

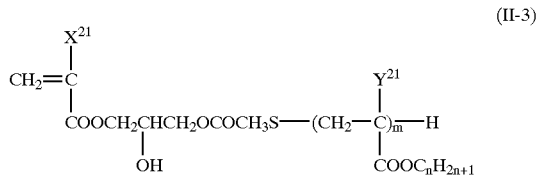

wherein $X^{21}$ and $Y^{21}$ are each a hydrogen atom or a methyl group; n is 1 to 22; and m is 5 to 100.

Specific examples of the macromonomer include the following:

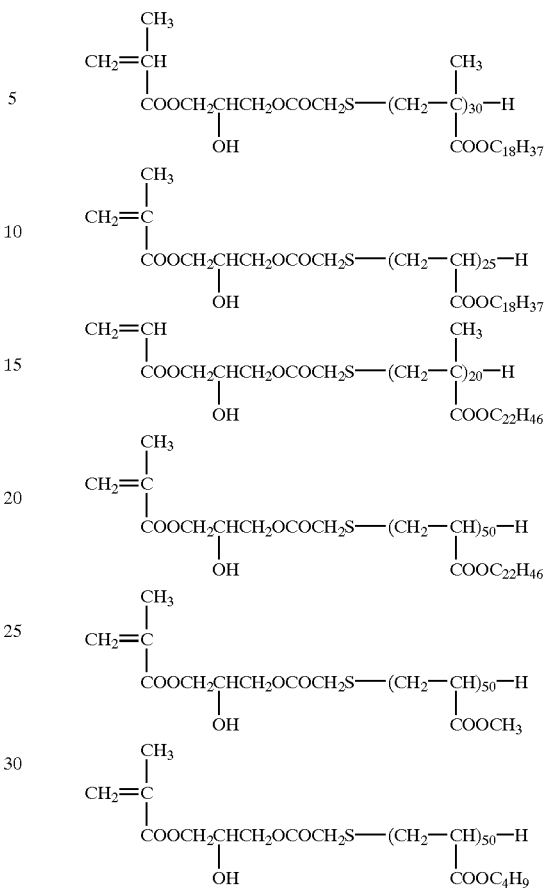

The $C_{1-4}$ alkyl group-containing alkyl (meth)acrylate has, for example, the following structural formula:

wherein X is a hydrogen atom or a methyl group; and n is 1 to 4.

Specific examples of the $C_{1-4}$ alkyl group-containing alkyl (meth)acrylate include methyl (meth)acrylate, ethyl (meth)acrylate, propyl (meth)acrylate, n-butyl (meth)acrylate, and t-butyl (meth)acrylate.

The $C_{1-22}$ alkyl group-containing alkyl (meth)acrylate, for example, the following structural formula:

wherein X is a hydrogen atom or a methyl group; and n is 1 to 22.

Specific examples of the $C_{1-22}$ alkyl group-containing alkyl (meth)acrylate include methyl (meth)acrylate, ethyl (meth)acrylate, propyl (meth)acrylate,, n-butyl (meth)acrylate, t-butyl (meth)acrylate, n-octyl (meth)acrylate, 2-ethylhexyl (meth)acrylate, dodecyl (meth)acrylate, cetyl (meth)acrylate, stearyl (meth)acrylate, and behenyl (meth)acrylate.

These fluorine-free monomers may be used in a combination of two or more of them.

In a copolymer comprising a fluorine-containing monomer (i.e., fluorine-containing (meth)acrylate) and a fluorine-free monomer, the content of the fluorine-containing monomer is 5 to 95% by weight, preferably 10 to 95% by weight, and most preferably 20 to 90% by weight. In the copolymer, as the proportion of the fluorine-free monomer increases, the pleasant feeling (i.e., slipperiness, nonstickiness, and the like) when used of the cosmetic containing the copolymer is enhanced and the solubility of the copolymer in a fluorine-free solvent becomes better. On the other hand, if the proportion of the fluorine-free monomer exceeds 95% by weight, it is impossible for the copolymer to impart sufficient oil repellency to the film.

In a copolymer comprising a fluorine-containing monomer and two types of fluorine-free monomers, for example, the weight ratio of the silicone macromonomer to the $C_{1-22}$ alkyl group-containing alkyl (meth)acrylate may be from 99:1 to 1:99, preferably range from 80:20 to 20:80. Meanwhile, the weight ratio of the silicone macromonomer to the alkyl (meth)acrylate macromonomer may be from 99:1 to 1:99, preferably from 80:20 to 20:80.

Other monomer may be used in combination with the above-mentioned monomers in order to enhance the feeling when used or in order to impart a function other than water resistance and water- and oil-repellency to the film. Specific examples of the other monomer include glycidyl (meth)acrylate, cyclohexyl (meth)acrylate, vinyl chloride, vinylidene chloride, and (meth)acrylic acid. The amount of the other monomer may be at most 20% by weight, for example, 0.1 to 10% by weight, based on the copolymer.

If the other monomer for combination is at least one selected from a monomer containing a hydrophilic group and/or a nitrogen-containing monomer, the resulting copolymer tends to be better adsorbed on the hair and therefore is suitable as a copolymer for use in hair care products or hair cosmetics.

Preferable as a copolymer for use in hair care products is one which comprises repeating units derived from (a) fluorine-containing (meth)acrylate, (b) silicone macromonomer, and (c) monomer containing a hydrophilic group and/or nitrogen-containing monomer. The weight ratio of (a): (b): (c) may be 10 to 90:10 to 90:0.1 to 20, preferably 20 to 80:20 to 80:0.1 to 10.

From the standpoint of the feeling of cosmetics when used, the particularly preferable Rf group of the fluorine-containing (meth)acrylate is a perfluoropolyether.

Examples of the monomer containing a hydrophilic group include (meth)acrylic acid and polyalkylene glycol (meth)acrylate.

The polyalkylene glycol (meth)acrylate may have the following formula:

$$CH_2=CR^{11}COO—(R^{12}—O)_n—R^{13} \qquad (II-2)$$

wherein $R^{11}$ and $R^{13}$ are each a hydrogen atom or a methyl group; $R^{12}$ is an alkylene group having 2 to 6 carbon atoms; and n is an integer 1 to 50.

Specific examples of the polyalkylene glycol (meth)acrylate include 2-hydroxyethyl (meth)acrylate, and $CH_2=C(CH_3)COO(CH_2CH_2O)_nH$ (wherein n is 2, 5 or 8).

Examples of the nitrogen-containing monomer include (meth)acrylamide, N,N-dimethylacrylamide, (meth)acrylonitrile, N-vinylpyrrolidone, dimethylaminoethyl (meth)acrylate, diethylaminoethyl (meth)acrylate, diacetone acrylamide, chloro-trimethylammonium ethyl(meth)acrylate, methacryloyloxyethyltrimethylammonium chloride, 2-hydroxy-3-methacryloyloxypropyltrimethylammonium chloride, and a monomer having at least one urethane or urea linkage.

Particularly preferred monomers are diacetone acrylamide and a monomer having at least one urethane or urea linkage.

Examples of the monomer having at least one urethane or urea linkage include bis(acryloyloxyethyl)hydroxyethyl isocyanurate, tris(acryloyloxyethyl) isocyanurate,

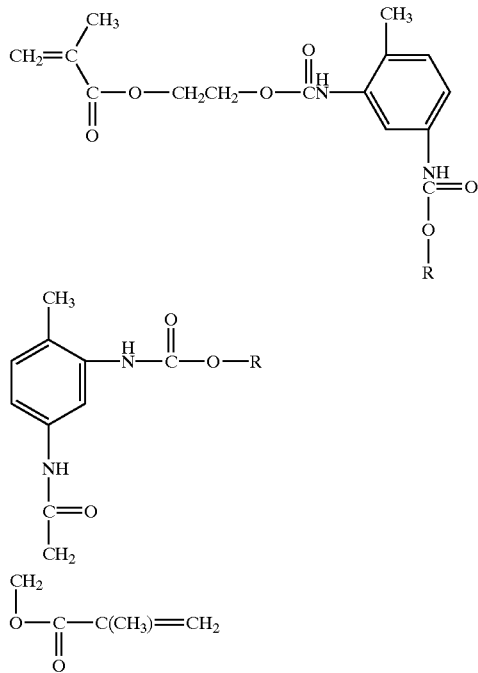

-continued

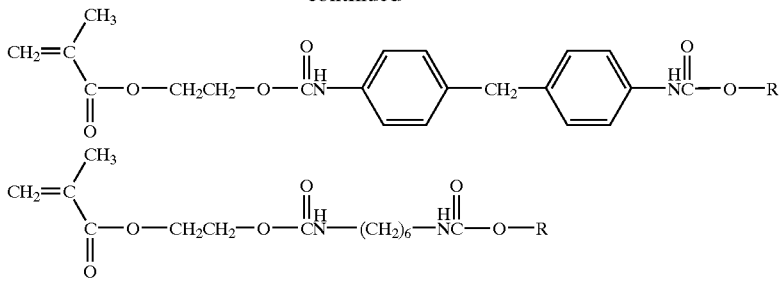

wherein R is an alkyl group having 1 to 22 carbon atoms.

The fluorine-containing copolymer of the present invention can be prepared by bulk polymerization, solution polymerization, or emulsion polymerization. According to the bulk polymerization, after the atmosphere surrounding a mixture of a fluorine-containing monomer and a fluorine-free monomer is replaced with nitrogen, the mixture is added with a polymerization initiator and stirred for several hours at a temperature in the range of from 40 to 80° C. to thereby carry out the polymerization. According to the solution polymerization, after a mixture of a fluorine-containing monomer and a fluorine-free monomer is dissolved in a suitable organic solvent capable of dissolving these monomers, the polymerization is carried out in a similar way. Examples of the organic solvent include a hydrocarbon-based solvent, an ester-based solvent, a ketone-based solvent, an alcohol-based solvent, a silicone-based solvent, and a fluorine-containing solvent.

According to the emulsion polymerization, after these monomers are emulsified in water by using a suitable emulsifier, the polymerization is carried out in a similar way. In several combinations of a fluorine-containing monomer and a fluorine-free monomer, the copolymerizability is poor because of poor compatibility between the fluorine-containing monomer and the fluorine-free monomer in water. In this case, a method, whereby the compatibility between the monomers is increased by the addition of a suitable auxiliary solvent such as a glycol or alcohol is adopted. The hydrophobic group of the emulsifier to be used in the emulsion polymerization may be hydrocarbon-based, silicone-based, or fluorine-containing. Likewise, the ionic character of the hydrophilic group may be nonionic, anionic, cationic, or amphoteric.

Examples of the polymerization initiator include an azo compound and a peroxide. When carrying out the polymerization, a chain transfer agent and a pH controlling agent may be added if necessary. The average molecular weight of the fluorine-containing copolymer obtainable after the polymerization is in the range of from 10,000 to 1,000,000, preferably in the range of from 20,000 to 300,000.

The reaction liquid containing the fluorine-containing copolymer prepared by solution polymerization or emulsion polymerization may be incorporated into a cosmetic. Alternatively, the copolymer is separated from the reaction liquid and the copolymer thus obtained may be dissolved (or dispersed) in a solvent (or water).

The fluorine-containing copolymer in the form of a single substance may be incorporated into a cosmetic. Preferably, however, the fluorine-containing copolymer is dissolved or dispersed in advance in water or in at least one material selected from a hydrocarbon-based solvent, an alcohol-based solvent, an ester-based solvent, an ketone-based solvent, a silicone-based solvent, and a fluorine-containing solvent, and the resultant solution or dispersion is provided as a raw material for a cosmetic. The proportion of the fluorine-containing copolymer based on the total [fluorine-containing copolymer+ (water or solvent)] may be 1 to 60% by weight, preferably 10 to 40% by weight. The proportion less than 1% by weight leads to insufficient amount of the fluorine-containing copolymer content in the cosmetic and therefore sufficient water resistance and water- and oil-repellency cannot be exhibited. On the other hand, the proportion more than 60% by weight lowers the stability as a material for the cosmetic.

The hair care product may contain the copolymer for use in the hair care product in an amount of 1 to 99% by weight, preferably in an amount of 2 to 50% by weight.

Examples of the hydrocarbon-based solvent include n-hexane, n-heptane, n-octane, n-nonane, n-decane, n-undecane, n-dodecane, isohexane, isoheptane, isooctane, isononane, isodecane, isoundecane, isododecane, cyclohexane, methylcyclohexane, cyclopentane, methylcyclopentane, liquid paraffin, isoparaffin, toluene, benzene, and xylene.

Examples of the ester-based solvent include butyl acetate, ethyl acetate, amyl acetate, and acyl acetate.

Examples of the ketone-based solvent include methyl ethyl ketone, methyl isobutyl ketone, and acetone.

Examples of the alcohol-based solvent include ethanol and isopropyl alcohol.

Examples of the silicone-based solvent include hexamethylcyclotrisiloxane (that is, cyclic silicone trimer), octamethylcyclotetrasiloxane (=cyclic silicone tetramer), decamethylcyclopentasiloxane (that is, cyclic silicone pentamer), dodecamethylcyclo-hexasiloxane (that is, cyclic silicone hexamer), dimethylpolysiloxane, methylphenyl-polysiloxane, and dimethylpolysiloxane/methyl (polyoxyethylene)siloxane/methyl(polyoxypropylene) siloxane copolymers.

Examples of the fluorine-containing solvent include hydrofluorocarbon (HFC), hydrofluoroether (HFE), fluoroether, fluorocarbon (FC), and nitrogen-containing fluorocarbon.

Examples of HFC include 1,1,1,2,2,3,4,5,5,5-decafluoropentane (HFC-4310), benzotrifluoride, and m-xylenehexafluoride.

HFE is represented by the general formula:

$$C_nH_mF_lOC_xH_yF_z$$

wherein n is a number of 1 to 12, m is a number of 0 to 25, 1 is a number of 0 to 11, m+1 is equal to 2n+1, x is a number of 1 to 12, y is a number of 0 to 25, z is a number of 0 to 11, and y+z is equal to 2x+1, with the proviso that m and y are not simultaneously 0 and that 1 and z are not simultaneously 0.

Specific examples of HFE include $C_4F_9OCH_3$ and $C_4F_9OC_2H_5$.

The fluoroether is represented by the general formula:

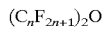
$(C_nF_{2n+1})_2O$ wherein n is a number of 3 to 5.

Specific examples of the fluoroether include $(C_3F_7)_2O$ and $(C_4F_9)_2O$.

Examples of FC include perfluorohexane, perfluorooctane, perfluorononane, perfluorobenzene, perfluorotoluene, perfluoroxylene, perfluorodecalin, and perfluoromethyldecalin.

The nitrogen-containing fluorocarbon is represented by the general formula:

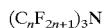
$(C_nF_{2n+1})_3N$ wherein n is a number of 1 to 5.

Specific examples of the nitrogen-containing fluorocarbon include perfluorotripropylamine and perfluorotributylamine.

These solvents may be used alone or in a combination of two or more of them. As for the solvents, a solvent which easily evaporates at the skin temperature (about 30° C.) is preferable because such a solvent makes the skin feel refreshed and facilitates the film formation on the skin. It is particularly preferable to use silicone-based solvents, such as octamethylcyclotetrasiloxane (that is, cyclic silicone tetramer), decamethylcyclopentasiloxane (that is, cyclic silicone pentamer), and dimethylpolysiloxane having a viscosity of at most 10 cSt, and hydrocarbon-based solvents such as isoparaffin. As for the fluorine-containing solvents, it is most preferable to use HFE such as $C_4F_9OCH_3$, $C_4F_9OC_2H_5$, $C_4F_9OC_3H_7$ or $C_4F_9$. This solvent is advantageous in that it is volatile and in that it is soluble in many of solvents and oils generally used in cosmetics and further in that it is a very good solvent for a fluorine-containing polymer.

The cosmetic of the present invention may contain 0.1 to 30% by weight of the fluorine-containing copolymer as an essential ingredient and may contain at least 0.1% by weight of a fluorine-containing compound-treated powder and/or a fluorine-containing oil.

Further, in the cosmetic of the present invention, the fluorine-containing copolymer may act as a compatibilizer or dispersant and compatibilizes or disperses the fluorine-containing compound-treated powder and/or fluorine-containing oil with or in a fluorine-free compound.

The fluorine-containing oil may be a perfluoropolyether, a hydrofluoroether, or a compound represented by the general formula:

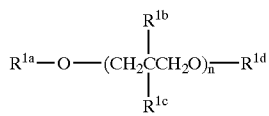

wherein $R^{1a}$ and $R^{1d}$ are each a hydrogen atom or a partially or completely fluorinated aliphatic group having 1 to 20 carbon atoms; $R^{1b}$ and $R^{1c}$ are each a hydrogen atom, or an aliphatic group having 1 to 20 carbon atoms, or a partially or completely fluorinated aliphatic group having 1 to 20 carbon atoms, with the proviso that at least one of $R^{1a}$ to $R^{1d}$ is a partially or completely fluorinated aliphatic group having 1 to 20 carbon atoms; and n is a number of 1 to 20, or by the general formula:

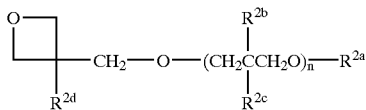

wherein $R^{2a}$ is a hydrogen atom or a partially or completely fluorinated aliphatic group having 1 to 20 carbon atoms; $R^{2b}$, $R^{2c}$ and $R^{2d}$ are each an aliphatic group having 1 to 20 carbon atoms or a partially or completely fluorinated aliphatic group having 1 to 20 carbon atoms, with the proviso that at least one of $R^{2a}$ to $R^{2d}$ is a partially or completely fluorinated aliphatic group having 1 to 20 carbon atoms; and m is a number of 1 to 20.

The raw materials to be used in the cosmetic of the present invention mixed with a fluorine-containing copolymer are not particularly limited in so far as these raw materials are those usually used for cosmetics.

Examples of the powder include inorganic powders such as talc, kaolin, mica, micaceous titanium, titanium oxide, iron oxide, magnesium oxide, zinc monoxide, zinc dioxide, heavy or light calcium carbonate, secondary calcium phosphate, aluminum hydroxide, barium sulfate, silica, alumina, silica gel, carbon black, antimony oxide, magnesium silicate aluminate, magnesium metasilicate aluminate and synthetic mica; and organic powders such as protein powder, fish scale foil, metal soap, polyvinyl chloride, nylon 12, fine crystalline fiber powder, tar dyes and lakes. These may be in an untreated state or may be treated with a silicone or a fluorine-containing compound. For example, the powder may be powder treated with a fluorine-containing compound.

Examples of non-powdery materials usable include solid or semi-solid oils such as vaseline, lanolin, serecin, microcrystalline wax, camauba wax, candelilla wax, higher fatty acids and higher alcohols; fluid oils such as sqaulene, fluid paraffin, ester oils, diglycerides, triglycerides and silicone oils; fluorine-containing oils such as perfluoropolyether, perfluorodecalin and perfluorooctane; water-soluble polymers and oil-soluble polymers; surfactants; colorants such as organic dyes; ethanol; and other additives such as antiseptics, antioxidants, coloring agents, thickeners, pH adjusting agents, perfumes, ultraviolet absorbers, moisturizers, blood circulation promoters, agents for giving cool-feeling, antiperspirants, bactericides and skin-activating agents.

The cosmetic of the present invention can be prepared according to a usually employed process and can be used as a makeup product such as foundation, face powder, cheek color, eye color, mascara, eyelash liner, and nail color; skin care products such as lotion and cream; and hair care products such as shampoo and rinse.

The copolymer of the present invention for cosmetics can be used to alleviate the following drawbacks of the fluorine-containing compound-treated powder.

poor affinity for a fluorine-free material, unsatisfied feeling such as inferior spreadability and adhesion when used, dust formation when the cosmetics are prepared, and poor dispersibility in a fluorine-free solvent In this case, the fluorine-containing compound-treated powder to be treated may be the powder which is treated with a fluorine-containing phosphate ester having, for example, the following general formula:

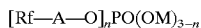

wherein Rf is a polyfluoroalkyl group having 6 to 16 carbon atoms or a perfluoropolyether group; A is an alkylene group having 1 to 4 carbon atoms,

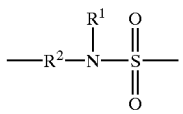

(wherein $R^1$ is an alkyl group having 1 to 4 carbon atoms and $R^2$ is an alkylene group having 1 to 4 carbon atoms), or

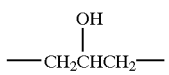

M is a hydrogen atom, a metal atom, ammonium, or substituted ammonium; and n is a number of 1 to 3.

Examples of the fluorine-containing compound-treated powder include powder which is treated with 3 to 7% by weight of a perfluoroalkyl phosphate ester diethanolamine salt.

Examples of the fluorine-containing compound-treated powder include inorganic or organic powder which is treated with a fluorine-containing compound. At the time when the powder is treated a copolymer, a mixture comprising two or more of the powders may be used. Furthermore, at the time when the treated powders are incorporated into cosmetics, a mixture of two or more of the treated powders may be used.

The copolymer for a cosmetic is adhered by either a wet process or a dry process to the surface of the fluorine-containing compound-treated powder. A wet process is preferable in order to carry out a more uniform surface treatment. More specifically, the process of the treatment comprises blending the fluorine-containing compound-treated powder with the copolymer as such or with a solution prepared by diluting a solution of the copolymer with an organic solvent, and stirring the mixture at room temperature or under heating until the fluorine-containing compound-treated powder is completely wetted with the solution in an organic solvent. For the purpose of the stirring, a stirring apparatus, such as a Henschel mixer, a vibration-type ball mill, a rotation-type ball mill, a super mixer, or a planetary mixer, can be used. When the stirring is carried out in a laboratory scale, a juice mixer for home use may be employed. Although the concentration of the copolymer in the solution in an organic solvent is not particularly limited, it is necessary to adjust the viscosity in order not to allow the viscosity to become excessively high when the solution is blended with the powder. Upon completion of the stirring, the organic solvent is removed either by vacuum or heating and thereafter the treated powder is dispersed uniformly in the stirring apparatus. When the stirring is carried out in a laboratory scale, a juice mixer for home use or a speed cutter may be employed.

The copolymer for cosmetics of the present invention can be used for the improvement of the water resistance and oil repellency of the silicone-treated powder. Examples of the silicone-treated powder include powder treated with methylhydrogenpolysiloxane in a wet process and powder treated with 1,3,5,7-tetramethylcyclotetrasiloxane in a chemical vapor deposition process. Examples of the powder to be treated with the silicone include talc, kaolin, mica, micaceous titanium, titanium oxide, iron oxide, and zinc dioxide, which powders are listed previously as powders to be treated with fluorine-containing compounds and used generally in cosmetics. At the time when the silicone-treated powder is treated with a copolymer, a mixture comprising two or more of the powders may be used. Furthermore, at the time when the treated powders are incorporated into cosmetics, a mixture of two or more of the silicone-treated powders may be used.

As in the case of the aforementioned powder treated with a fluorine-containing compound, the copolymer for a cosmetic is adhered by either a wet process or a dry process to the surface of the silicone-treated powder. However, the wet process is preferable in order to carry out a more uniform surface treatment.

If necessary, at the time of surface treatment in the present invention, a suitable chemical substance may be used in order to improve the feeling when used. Examples of the chemical substance for the improvement of the feeling of cosmetics powder when used include lecithin, n-mono-long-chain-acyl basic amino acid, silicone, chitosan, collagen and wax.

Heretofore, the affinity of a fluorine-containing oil, which is represented by a perfluoropolyether, for a fluorine-free material is so poor that it has been difficult to incorporate the above-described fluorine-containing material in a cosmetic. After extensive studies to overcome the above problem, the present inventors have facilitated the incorporation by using a fluorine-containing oil/fluorine-free solvent type nonaqueous emulsion which is prepared by emulsifying a fluorine-containing oil in a fluorine-free solvent, such as a silicone-based solvent, a hydrocarbon-based solvent, an ester-based solvent and a ketone-based solvent, by using as an emulsifier a fluorine-containing (meth)acrylate copolymer having specific ingredients.

Further, the present invention provides a cosmetic containing a nonaqueous emulsion, which is prepared by emulsifying a fluorine-containing oil in a fluorine-free solvent by using as an emulsifier the copolymer for cosmetic, wherein:
the copolymer for cosmetic comprises
(1) a fluorine-containing (meth)acrylate and a silicone macromonomer,
(2) a fluorine-containing (meth)acrylate and a polyalkylene glycol (meth)acrylate, or
(3) a fluorine-containing (meth)acrylate, a silicone macromonoer, and an alkyl (meth)acrylate macromonomer;
the fluorine-free solvent is a silicone-based solvent, a hydrocarbon-based solvent, an ester-based solvent, or a ketone-based solvent; and
the fluorine-containing oil is a perfluoropolyether, a hydrofluoroether, or a compound represented by the general formula:

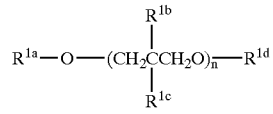

wherein $R^{1a}$ and $R^{1d}$ are each a hydrogen atom or a partially or completely fluorinated aliphatic group having 1 to 20 carbon atoms; $R^{1b}$ and $R^{1c}$ are each a hydrogen atom, an aliphatic group having 1 to 20 carbon atoms, or a partially or completely fluorinated aliphatic group having 1 to 20 carbon atoms, with the proviso that at least one of $R^{1a}$ to $R^{1d}$ is a partially or completely fluorinated aliphatic group having 1 to 20 carbon atoms; and n is a number of 1 to 20, or by the general formula:

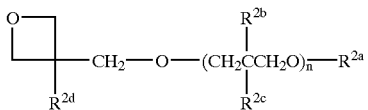

wherein $R^{2a}$ is a hydrogen atom or a partially or completely fluorinated aliphatic group having 1 to 20 carbon atoms; $R^{2b}$, $R^{2c}$ and $R^{2d}$ are each an aliphatic group having 1 to 20 carbon atoms or a partially or completely fluorinated aliphatic group having 1 to 20 carbon atoms, with the proviso that at least one of $R^{2a}$ to $R^{2d}$ is a partially or completely fluorinated aliphatic group having 1 to 20 carbon atoms; and m is a number of 1 to 20.

The amount of the emulsifier may be 1 to 50 parts by weight, for example, 5 to 20 parts by weight, based on 100 parts by weight of the fluorine-containing oil. The amount of the fluorine-free solvent may be 50 to 10,000 parts by weight, for example, 100 to 1,000 parts by weight, based on 100 parts by weight of the fluorine-containing oil.

When a fluorine-containing oil is to be emulsified in a silicone-based solvent, a copolymer comprising a fluorine-containing (meth)acrylate and a silicone macromonomer is the most suitable as the emulsifier. This is because the copolymer is adsorbed on the fluorine-containing oil/silicone-based solvent interface so that the interfacial tension is remarkably reduced and the fluorine-containing oil is prevented from being flocculated and collected.

Meanwhile, when a fluorine-containing oil is to be emulsified in a hydrocarbon-based solvent, an ester-based solvent or a ketone-based solvent, a copolymer comprising a fluorine-containing (meth)acrylate and an alkyl (meth) acrylate macromonomer is the most suitable as the emulsifier because of the same reason as that described above. In this case, if the chain length of the alkyl group of the alkyl (meth)acrylate macromonomer is properly selected in accordance with the type of the fluorine-free solvent, a stable nonaqueous emulsion can be prepared more effectively. More specifically, a $C_{12-22}$ alkyl (meth)acrylate macromonomer is preferable when the fluorine-free solvent is a hydrocarbon-based solvent, while a $C_{1-4}$ alkyl (meth) acrylate macromonomer is preferable when the fluorine-free solvent is an ester-based solvent or a ketone-based solvent.

A copolymer comprising a fluorine-containing (meth) acrylate, a silicone macromonomer and an alkyl (meth) acrylate macromonomer is the most preferable, when the fluorine-free solvent is a mixer of a silicone-based solvent, a hydrocarbon-based solvent, an ester-based solvent and a ketone-based solvent.

Generally, when a large amount of an oil-soluble polymer is incorporated in a cosmetic, the polymer is previously dissolved in a volatile solvent and the solution thus obtained is incorporated in the cosmetic. This procedure is employed because the oil-soluble polymer is in a solid or elastic rubbery state and therefore the polymer is not easily incorporated in the cosmetic. The volatile solvent, represented by a cyclic silicone or iso-paraffin, is a good solvent for the oil-soluble polymer and can impart a high function to the cosmetic. However, since such a volatile solvent is so irritant to the skin that it cannot be used in a cosmetic which is sensitive to the skin and therefore needs to be less irritant to the skin. For this reason, there has been a demand for an oil-soluble polymer which is in a pasty state and can be easily incorporated in the cosmetic. The term "pasty state" is used herein to mean a rheological property which is not fluid but can be easily spread on the skin by the force of a hand at room temperature.

Although most of the copolymers are solid or rubbery in the present invention, the present inventors have found that a (meth)acrylate copolymer having specific ingredients is in a pasty state after extensive studies to solve the above-mentioned problem.

Furthermore, the present invention provides a cosmetic comprising a copolymer comprising a fluorine-containing (meth)acrylate and a silicone macromonomer, wherein the weight ratio of the fluorine-containing (meth)acrylate to the silicone macromonomer is 3/7 to 7/3 and the copolymer is a pasty substance and wherein a volatile solvent is not incorporated.

As to the ingredients of the copolymer, the weight ratio of the fluorine-containing (meth)acrylate to the silicone macromonomer may be 3/7 to 7/3, for example, 4/6 to 6/4. The pasty property can be changed by the incorporation of a proper amount of a solid or rubbery polymer in the copolymer. The amount of the pasty copolymer may be 1 to 100% by weight, for example, 2 to 80% by weight, based on the total amount of the cosmetic.

Except for the feature that the pasty copolymer is used as an essential ingredient and any volatile solvent is not incorporated, raw materials which are usually used for cosmetics can also be used in the present invention. For example, besides the copolymer, at least one material selected from powder, an oil having a high boiling point, a solid oil, water, a water-soluble polymer, an emulsifier and a moisturizer may be incorporated in, the cosmetic of the present invention.

The selection of a fluorine-containing copolymer prepared by polymerizing the fluorine-containing (meth) acrylate and the silicone macromonomer provides satisfactory water resistance and water- and oil-repellency which derive from the fluorine-containing (meth)acrylate and satisfactory water resistance, water- and oil-repellency, and feeling when used (i.e., slipperiness, nonstickiness, and the like) which derive from the silicone macromonomer. In addition, the use of the silicone macromonomer in copolymerization increases the solubility of the copolymer in silicone oils generally used in cosmetics. If such a copolymer is used in a cosmetic incorporated with a large amount of the fluorine-containing raw material and the silicon-containing raw material, the copolymer acts as a compatibilizer and thus increases the stability of the cosmetic.

Further, the selection of a fluorine-containing copolymer prepared by polymerizing an alkyl (meth)acrylate or an alkyl (meth)acrylate macromonomer in addition to the fluorine-containing (meth)acrylate and the silicone macromonomer can improve the solubility in a hydrocarbon-based solvent, an ester-based solvent or a ketone-based solvent. In particular, the copolymer, which is produced by using an alkyl (meth)acrylate macromonomer, is a graft copolymer comprising fluorine-containing (meth)acrylate segments, silicone segments and alkyl (meth)acrylate segments. The graft copolymer thus obtained exhibits improved solubility in a solvent and provides higher water resistance and water- and oil-repellency at a lower fluorine concentration in comparison with a copolymer produced by using an alkyl (meth)acrylate. If such a graft copolymer is used in a cosmetic incorporated with a fluorine-containing raw material, a silicon-containing raw material, and a hydrocarbon-based solvent, an ester-based solvent or a ketone-based solvent, the graft copolymer acts as a compatibilizer and thus increases the stability of the cosmetic.

Furthermore, the selection of a fluorine-containing copolymer prepared by radically polymerizing the fluorine-containing (meth)acrylate and the polyalkylene glycol (meth)acrylate can prevent the makeup from destruction even in an environment where sweat and skin fat are simultaneously present.

Generally, the surface of a fluorine-containing copolymer, which comprises no hydrophilic monomer, repels oil when the surface is dry but becomes wetted with the oil if water is simultaneously present ("Surface Properties and Application of Fluoroalkyl Acrylate Polymers", Motonobu KUBO, Surface, 33, 185(1955)). This problem can be solved by introducing a hydrophilic monomer, particularly polyethylene glycol (meth)acrylate, into the copolymer by way of copolymerization. On the skin, the amount of sweat and skin fat varies depending on the surrounding environments. The fluorine-containing copolymer containing polyethylene glycol (meth)acrylate exhibits water- and oil-repellency in any environment whatsoever. However, the water resistance of the copolymer comprising such a monomer tends to be somewhat reduced.

The Preferred Embodiments of the Invention

The present invention is more specifically illustrated by the following examples, although it should be understood that the present invention is not restricted to these examples.

Preparative Example 1

20 g of $CH_2=CHCOO(CH_2)_2(CF_2CF_2)_nCF_2CF_3$ (hereinafter abbreviated as "FA")(a mixture of compounds at a weight proportion of 5:3:1 wherein n is 3, 4, and 5), 20 g of a silicone macromonomer having the following formula:

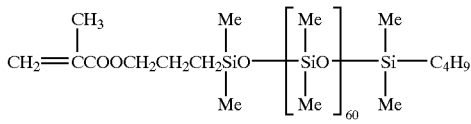

wherein Me is a methyl group [hereinafter abbreviated as "Si-MM", trade name SIRAPLENE FM-0721(molecular weight: 5,000), manufactured by Chisso Corp.], and 158 g of toluene were placed in a four-neck flask fitted with a reflux condenser, tube for introduction of nitrogen, thermometer, and stirrer. The reaction liquid was heated to 60° C. and stirred at that temperature for 30 minutes under a nitrogen stream. Then, the reaction liquid was added with 2 g of t-butyl peroxypivalate (trade name "PERBUTYL", manufactured by Nippon Oil & Fats Co. Ltd.) and the polymerization reaction was continued for 6 hours. The polymerization percentage of FA was found to be 95% by analyzing the proportion of FA remaining in the reaction liquid by gas chromatography. Next, a part of the reaction liquid was taken out and added to ethanol so as to cause precipitation. The precipitate thus obtained was collected and dried under vacuum. In this way, FA/Si-MM (=5/5 wt.) copolymer was separated. The molecular weight of the FA/Si-MM copolymer was measured by GPC. The weight average molecular weight was found to be 50,000 (in terms of polystyrene). The FA/Si-MM copolymer thus obtained was dissolved in a cyclic silicone pentamer so that the concentration of the FA/Si-MM copolymer in the liquid was adjusted to 20% by weight. In this way, a solution of FA/Si-M copolymer in a cyclic silicone pentamer (20% by weight) was obtained.

Preparative Example 2

A solution of FA/Si-MM (5/5 wt.) copolymer in a dimethylpolysiloxane (20% by weight) was obtained by carrying out preparation in the same manner as in Preparative Example 1, except that the cyclic silicone pentamer as a solvent for dilution was replaced by the dimethylpolysiloxane (100 cS).

Preparative Example 3

A FA/Si-MM (=8/2 wt.) copolymer was obtained by carrying out the polymerization and separation in the same manner as in Preparative Example 1, except that the monomers, i.e., 20 g of FA and 20 g of Si-MM, were replaced by 32 g of FA and 8 g of Si-MM. The FA/Si-MM copolymer thus obtained was dissolved in $C_4F_9OCH_3$ as a type of HFE so that the concentration of the FA/Si-MM copolymer in the solution was adjusted to 20% by weight. In this way, a solution of FA/Si-MM copolymer in HFE (20% by weight) was obtained.

Preparative Example 4

54 g of FA, 36 g of $CH_2=CHCOO(CH_2CH_2O)_nH$ (n=7 to 9) (BLENMER PE-350, manufactured by Nippon Oil & Fats Co. Ltd.) and 400 g of isopropanol were placed in a four-neck flask fitted with a reflux condenser, tube for introduction of nitrogen, thermometer and stirrer. The reaction liquid was heated to 80° C. and stirred at that temperature for 30 minutes under a nitrogen stream. Then, the reaction liquid was added with 1 g of azobis (isobutylamidinate) salt and the polymerization reaction was continued for 6 hours with stirring. The polymerization percentage of FA was found to be 99% or more by analyzing the proportion of FA remaining in the reaction liquid by gas chromatography. Next, a part of the reaction liquid was taken out and added with n-hexanol so as to cause precipitation. The precipitate thus obtained was collected and dried under vacuum. In this way, FA/PE-350 (=6/4 wt.) copolymer was separated. The molecular weight of the FA/PE-350 copolymer was measured by GPC. The weight average molecular weight was found to be 20,000 (in terms of polystyrene). The FA/PE-350 copolymer thus obtained was dissolved in ethanol so that the concentration of the FA/Si-MM copolymer in the solution was adjusted to 20% by weight. In this way, a solution of FA/PE-350 copolymer in ethanol (20% by weight) was obtained.

Preparative Example 5

A solution of FA/HEMA (=6/4 wt.) copolymer in ethanol (20% by weight) was obtained by carrying out preparation in the same manner as in Preparative Example 4, except that PE-350 as the monomer was replaced by 2-hydroxyethyl methacrylate (HEMA).

Preparative Example 6

36 g of FA, 24 g of n-butyl acrylate (BA), 90 g of ion-exchanged water, 24 g of ethanol, 0.06 g of n-lauryl mercaptan, 1.8 g of sorbitan monolaurate and 4.2 g of polyoxyethylene octyl phenyl ether were mixed together and heated to 60° C. Then, the mixture was emulsified using a high-pressure homogenizer. The emulsion thus obtained was placed in a four-neck flask fitted with a reflux condenser, tube for introduction of nitrogen, thermometer and stirrer. The reaction liquid was kept at 60° C. under a nitrogen stream and sufficiently stirred. Then, the reaction liquid was added with 0.3 g of azobis(isobutylamidine) dihydrochloride (trade name V-50 manufactured by Wako Pure Chemical Industries, Ltd.) and polymerization was initiated. The polymerization was carried out by keeping the reaction liquid at 60° C. for 3 hours with stirring to obtain a polymer emulsion. The polymerization percentage of FA was found to be 99% or more by analyzing the proportion of FA remaining in the reaction liquid by gas chromatography. Next, a part of the polymer emulsion was taken out and added with ethanol so as to cause precipitation. The precipitate thus obtained was collected and dried under vacuum. In this way, the polymer was separated. The molecular weight of the polymer was measured by GPC. The weight average molecular weight was found to be 200,000. Meanwhile, 5 g the polymer emulsion was kept at 130° C. for 2 hours to thereby measure the amount of the evaporation residue (this evaporation residue comprises the polymer and emulsifier and constitutes the effective ingredients of the emulsion). The concentration of the effective ingredients as calculated from the amount of the evaporation residue was 34% by weight. The polymer emulsion was diluted with ion-exchanged water so that the concentration of the effective ingredients was adjusted to 30% by weight. In this way, an FA/BA (=6/4 wt.) copolymer emulsion (30% by weight) was obtained.

Preparative Example 7

An FA/SMA-MM (=2/8 wt.) copolymer was obtained by carrying out polymerization and separation in the same manner as in Preparative Example 1, except that 20 g of FA and 20 g of Si-MM as monomers were replaced by 8 g of FA and 32 g of stearyl methacrylate macromonomer:

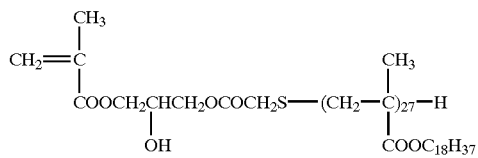

[hereinafter abbreviated as "SMA-MM", trade name MM-8SMA (molecular weight: 9,000), manufactured by Toagosei Chemical Industry Co., Ltd.]. The FA/SMA-MM copolymer thus obtained was dissolved in isoparaffin so that the concentration of the copolymer in the solution was adjusted to 20% by weight. In this way, a solution of FA/SMA-MM copolymer in isoparaffin (20% by weight) was obtained.

Preparative Example 8

A solution of FA/Si-MM/BA (5/2.5/2.5 wt.) copolymer in a cyclic silicone pentamer (20% by weight) was obtained by repeating the procedure of Preparative Example 1, except that 20 g of FA and 20 g of Si-MM as monomers were replaced by 20 g of FA, 10 g of Si-MM and 10 g of BA.

Preparative Example 9

An FA/Si-MM/SMA-MM (5/2.5/2.5 wt.) copolymer was obtained by carrying out polymerization and separation in the same manner as in Preparative Example 1, except that 20 g of FA and 20 g of Si-MM as monomers were replaced by 20 g of FA, 10 g of Si-MM and 10 g of SMA-MM. The FA/Si-MM/SMA-MM copolymer thus obtained was dissolved in a cyclic silicone pentamer so that the concentration of the copolymer in the solution was adjusted to 20% by weight. In this way, a solution of FA/Si-MM/SMA-MM copolymer in the cyclic silicone pentamer (20% by weight) was obtained.

Preparative Example 10

A solution of an FA-MM/Si-MM (=5/5 wt.) copolymer in a cyclic silicone pentamer (20% by weight) was obtained by carrying out preparation in the same manner as in Prepative Example 1, except that 20 g of FA as a monomer was replaced by 20 g of an FA macromonomer (FA-MM):

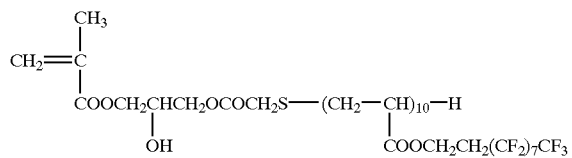

and 158 g of toluene was replaced by 79 g of perchloroethylene and 79 g of hydrochlorofluorocarbon 225.

Preparative Example 11

A solution of PFPE-A/Si-MM (5/5 wt.) copolymer in a cyclic silicone pentamer (20% by weight) was obtained by repeating the procedure of Prepative Example 1, except that 20 g of FA as a monomer was replaced by 20 g of perfluoropolyether acrylate $F(CF_2CF_2CF_2O)_{10}CF_2CF_2-CH_2CH_2OCOCH=CH_2$ (PFPE-A) and 158 g of toluene was replaced by 79 g of perchloroethylene and 79 g of hydrochlorofluorocarbon 225.

Comparative Preparative Example 1

A solution of Si-MM/MMA/BMA (=3/5/2 wt.) copolymer in a cyclic silicone pentamer (20% by weight) was obtained by repeating the procedure of Preparative Example 1, except that 20 g of FA and 20 g of Si-MM as monomers were replaced by 12 g of Si-MM, 20 g of methyl methacrylate (MMA) and 8 g of butyl methacrylate (BMA).

Comparative Preparative Example 2

An emulsion of EA/EMA (=8/2 wt.) copolymer (30% by weight) was obtained by repeating the procedure of Preparative Example 6, except that 36 g of FA and 24 g of BA as monomers were replaced by 48 g of ethyl acrylate (EA) and 12 g of ethyl methacrylate (EMA) and the initiator V-50 was replaced by potassium persulfate.

Comparative Preparative Example 3

An emulsion of FA/StA (=6/4 wt.) copolymer (30% by weight) was obtained by repeating the procedure of Preparative Example 6, except that 24 g of BA as a monomer was replaced by 24 g of stearyl acrylate (EA).

Comparative Preparative Example 4

A solution of FA/SMA (=2/8 wt.) copolymer in isoparaffin (20% by weight) was obtained by repeating the procedure of Preparative Example 7, except that 32 g of SMA-MM as a monomer was replaced by 32 g of stearyl methacrylate (SMA).

EXAMPLE 1

Films were formed by casting each of the polymer liquids obtained in Preparative Examples 1 to 11 and Comparative Preparative Examples 1 to 4 on a smooth polyester film and allowing the coating to stand for one day. The films were evaluated in terms of water- and oil-repellency and water resistance. The results are shown in Table 1.

The water- and oil-repellency was assessed by the contact angle with water (water-repellency) or a fluid paraffin (oil-repellency). The contact angle of 110 to 130° was rated as ⊚, the contact angle of 90 to 109° as ○:, the contact angle of 60 to 89° as Δ, the contact angle of 30 to 59° as x, and the contact angle of 29° or less as xx. The water resistance was assessed by the contact angle of the film which had been allowed to stand for one day after being immersed in water for one hour. The experiments of water- and oil-repellency and water resistance were conducted at 25° C.

x: poor
xx: bad

The assessment was conducted by a panel of 5 members specialized in sensory evaluation (with the exception that the stability and dispersibility were assessed by one chemist specialized in cosmetics) and the average of the ratings by the members was taken as a result. As in Example 1, films were formed by coating each of the polymer liquids uniformly on a smooth polyester film and allowing the coating to stand for one day. The films were then immersed in water for one hour and thereafter allowed to stand for one day. Then, the contact angle was measured and assessed according to the same criterion as in Example 1.

TABLE 1

Water resistance, and water- and oil-repellency of film forming agents

| Preparative Example | Ingredients of Polymer (weight ratio) | Solvent for dilution | Water repellency | Oil repellency | Water resistance |
|---|---|---|---|---|---|
| 1 | FA/Si-MM = 5/5 | Cyclic silicone pentamer | ⊚ | ○ | ⊚ |
| 2 | FA/Si-MM = 5/5 | Dimethylpolysiloxane | ⊚ | ○ | ⊚ |
| 3 | FA/Si-MM = 8/2 | HFE | ⊚ | ○ | ⊚ |
| 4 | FA/PE-350 = 6/4 | Ethanol | ⊚ | ○ | Δ |
| 5 | FA/HEMA = 6/4 | Ethanol | ⊚ | ○ | ○ |
| 6 | FA/BA = 6/4 | Water | ⊚ | ○ | ⊚ |
| 7 | FA/SMA-MM = 2/8 | Isoparaffin | ⊚ | ○ | ⊚ |
| 8 | FA/Si-MM/BA = 5/2.5/2.5 | Cyclic silicone pentamer | ⊚ | ○ | ⊚ |
| 9 | FA/Si-MM/SMA-MM = 5/2.5/2.5 | Cyclic silicone pentamer | ⊚ | ○ | ⊚ |
| 10 | FA-MM/Si-MM = 5/5 | Cyclic silicone pentamer | ⊚ | ○ | ⊚ |
| 11 | PEPE-A/Si-MM = 5/5 | Cyclic silicone pentamer | ⊚ | ○ | ⊚ |
| Comparative Preparative Example1 | Si-MM/MMA/BMA = 3/5/2 | Cyclic silicone pentamer | ⊚ | xx | ○ |
| Comparative Preparative Example2 | EA/EMA = 8/2 | Water | x | xx | x |
| Comparative Preparative Example3 | FA/StA = 6/4 | Water | ⊚ | xx | x |
| Comparative Preparative Example4 | FA/SMA = 2/8 | Isoparaffin | ⊚ | xx | Δ |

In the following Examples and Comparative Examples, cosmetics were each prepared using blend powder shown in Table 2. The fluorine-treated powders (1) to (6) indicate powders treated with 5% perfluoroalkylethyl phosphate ester diethanol amine salt. The silicone-treated powders (7) to (9) indicate powders treated with 2% methylhydrogenpolysiloxane.

TABLE 2

Ingredients of blend powder

| Type of raw material | % by weight |
|---|---|
| (1) Fluorine-treated titanium oxide | 8.0 |
| (2) Fluorine-treated yellow iron oxide | 0.9 |
| (3) Fluorine-treated red iron (III) oxide | 0.3 |
| (4) Fluorine-treated black iron oxide | 0.3 |
| (5) Fluorine-treated talc | 28.7 |
| (6) Fluorine-treated sericite | 31.5 |
| (7) Silicone-treated talc | 3.8 |
| (8) Silicone-treated sericite | 19.1 |
| (9) Silicone-treated mica | 7.4 |

Durability of makeup (derived from the water- and oil-repellency of film), feeling when used (slipperiness and nonstickiness), hairdressing power, feeling of touch, stability (at 50° C. for one month), dispersibility (at 50° C. for one month), and water resistance were assessed according to the following criterion:

⊚: very good
○: good
Δ: moderate

EXAMPLES 2 AND 3

Powdery foundations were prepared according to the formulations shown in Table 3. In the preparation, ingredients (1) and (2) were mixed and crushed in an atomizer. The blend was then placed in a Henschel mixer and ingredients (3) to (5) were also placed in the mixer. The ingredients in the mixer were uniformly mixed. The blend was then placed in a mold and press-molded to thereby form a powdery foundation. The durability, water resistance, and feeling when used of the makeup by the powdery foundation were assessed. The results are shown in Table 3.

TABLE 3

Powdery foundations

| Name of raw material | Example 2 | Example 3 |
|---|---|---|
| (1) Blend powder | 89.8 | 89.8 |
| (2) Paraoxybenzoate ester | 0.1 | 0.1 |
| (3) Solution of FA/SI-MM (= 5/5 wt.) copolymer in cyclic silicone pentamer (20% by weight) (Preparative Example 1) | 10.0 | — |

TABLE 3-continued

Powdery foundations

| Name of raw material | Example 2 | Example 3 |
|---|---|---|
| (4) Solution of FA/Si-MM (= 5/5 wt.) copolymer in dimethylpolysiloxane (20% by weight) (Preparative Example 2) | — | 10.0 |
| (5) Perfume | 0.1 | 0.1 |
| Durability | ⊚ | ⊚ |
| Water resistance | ⊚ | ⊚ |
| Feeling when used | ⊚ | ⊚ |

The numerals in the table indicate weight percent.

EXAMPLE 4

The fluorine-treated powders (1) to (6), which were constituents of the blend powder shown in Table 2, were surface-treated with the FA/Si-MM (=5/5 wt.) copolymer of Preparative Example 1 in the following way. 40 g of a mixture comprising the fluorine-treated powders (1) to (6) and 10 g of a solution of FA/Si-MM (=5/5 wt.) copolymer in cyclic silicone pentamer (20% by weight) were mixed together in a juice mixer for 30 seconds. The mixture was placed in an aluminum vat and dried at 60° C. for 24 hours. After being dried, the mixture was crushed by a speed cutter to thereby obtain powder surface-treated with the FA/Si-MM copolymer.

Next, a powdery foundation was prepared by carrying out the same procedure as in Example 3, except that the blend powder in an amount of 89.8% by weight containing 69.7% by weight of the fluorine-treated powders (1) to (6) was replaced by the blend powder in an amount of 89.8% by weight containing 69.7% by weight of the fluorine-treated powder which was further surface-treated with the FA/Si-MM copolymer, and the solution of FA/Si-MM copolymer in a dimethylpolysiloxane (20% by weight) in an amount of 10% by weight was replaced by 10% by weight of dimethylpolysiloxane. The fluorine-treated powder which was surface-treated with the FA/Si-MM copolymer prior to incorporation in a cosmetic enabled the cosmetic to exhibit better durability and water resistance of makeup in comparison with Example 3.

EXAMPLES 5 AND 6

Liquid foundations (oily) were prepared according to the formulations shown in Table 4. In the preparation, ingredients (1) to (6) were uniformly mixed in a colloid mill to thereby obtain a liquid foundation. The durability, water resistance, and feeling of the makeup at usage were assessed for the liquid foundation. The results are shown in Table 4.

TABLE 4

Liquid foundations (Oily)

| Name of raw material | Example 5 | Example 6 |
|---|---|---|
| (1) Solution of FA/Si-MM/BA (= 5/2.5/2.5 wt.) copolymer in cyclic silicone pentamer (20% by weight) (Preparative Example 8) | 25 | — |
| (2) Solution of FA/Si-MM/SMA-MM (= 5/2.5/2.5 wt.) copolymer in cyclic silicone pentamer (20% by weight) (Preparative Example 9) | — | 25.0 |
| (3) Cyclic silicone pentamer | 48.9 | 48.9 |
| (4) Anhydrous silica | 6.0 | 6.0 |
| (5) Blend powder | 20.0 | 20.0 |
| (6) Perfume | 0.1 | 0.1 |
| Durability | ⊚ | ⊚ |
| Water resistance | ⊚ | ⊚ |
| Feeling when used | ⊚ | ⊚ |

The numerals in the table indicate weight percent.

EXAMPLES 7 TO 10 AND COMPARATIVE EXAMPLE 1

Liquid foundations (O/W types) were prepared according to the formulations shown in Table 5. In the preparation, ingredients (1) to (8) were mixed and crushed in a colloid mill. The blend was then heated to 80° C. and added with ingredients (8) to (13) which had been mixed under heating. These ingredients were uniformly emulsified by a homogenizing mixer. The emulsion was added with ingredients (14) to (19) and the ingredients were further uniformly emulsified in the homogenizing mixer to thereby form a liquid foundation. The durability, water resistance and feeling of the makeup at usage were assessed for the liquid foundation. The results are shown in Table 5.

TABLE 5

Liquid foundations (O/W types)

| Name of raw material | Example 7 | Example 8 | Example 9 | Example 10 | Comparative Example 1 |
|---|---|---|---|---|---|
| (1) 1, 3-butylene glycol | 10.00 | 10.00 | 10.00 | 10.00 | 10.00 |
| (2) Carboxymethyl cellulose | 0.20 | 0.20 | 0.20 | 0.20 | 0.20 |
| (3) Aluminum magnesium silicate | 0.20 | 0.20 | 0.20 | 0.20 | 0.20 |
| (4) Blend powder | 14.00 | 14.00 | 14.00 | 14.00 | 14.00 |
| (5) Purified water | 50.65 | 50.65 | 50.65 | 50.65 | 50.65 |
| (6) Sodium N-stearoyl-L-glutaminate | 0.75 | 0.75 | 0.75 | 0.75 | 0.75 |
| (7) Potassium hydroxide | 0.40 | 0.40 | 0.40 | 0.40 | 0.40 |
| (8) Paraoxybenxoate ester | 0.20 | 0.20 | 0.20 | 0.20 | 0.20 |
| (9) Glyceryl trioctanoate | 5.00 | 5.00 | 5.00 | 5.00 | 5.00 |

TABLE 5-continued

Liquid foundations (O/W types)

| Name of raw material | Example 7 | Example 8 | Example 9 | Example 10 | Comparative Example 1 |
|---|---|---|---|---|---|
| (10) Diisostearyl malate | 3.00 | 3.00 | 3.00 | 3.00 | 3.00 |
| (11) Stearic acid | 3.00 | 3.00 | 3.00 | 3.00 | 3.00 |
| (12) Stearic acid monoglyceride | 1.50 | 1.50 | 1.50 | 1.50 | 1.50 |
| (13) Cetanol | 1.00 | 1.00 | 1.00 | 1.00 | 1.00 |
| (14) Solution of FA/PE-350 (= 6/4 wt.) copolymer in ethanol (20% by weight) (Preparative Example 4) | 10.00 | — | — | — | — |
| (15) Solution of FA/HEMA (= 6/4 wt.) copolymer in ethanol (20% by weight) (Preparative Example 5) | — | 10.00 | — | — | — |
| (16) Solution of FA-MM/Si-MM (= 5/5 wt.) copolymer in cyclic silicone pentamer (20% by weight) (Preparative Example 10) | — | — | 10.00 | — | — |
| (17) Solution of PFPE-A/Si-MM (= 5/5 wt.) copolymer in cyclic silicone pentamer (20% by weight) (Preparative Example 11) | — | — | — | 10.00 | — |
| (18) Solution of Si-MM/MMA/BMA (= 3/5/2 wt.) copolymer in cyclic silicone pentamer (20% by weight) (Comparative preparative Example 1) | — | — | — | — | 10.00 |
| (19) Perfume | 0.10 | 0.10 | 0.10 | 0.10 | 0.10 |
| Durability | ⊚ | ⊚ | ○ | ○ | Δ |
| Water resistance | Δ | ○ | ⊚ | ⊚ | ○ |
| Feeling when used | ○ | ○ | ⊚ | ⊚ | ⊚ |

The numerals in the table indicate weight percent.

EXAMPLE 11 AND COMPARATIVE EXAMPLES 2 AND 3

Mascara was prepared according to the formulations shown in Table 6. In the preparation, ingredients (1) to (7) were heated to 80° C. and added with ingredients (12) to (15) which had been mixed and heated at 80° C. The mixture was uniformly emulsified by a homogenizing mixer. The emulsion was added with ingredients (8) to (11), which had been passed through a three-roller mill three times in advance, and with ingredients (16) to (18). The mixture was then cooled to room temperature. In this way, mascara was obtained. The durability, water resistance, and feeling when used of the makeup by the mascara were assessed. The results are shown in Table 6.

TABLE 6

Mascara

| Name of raw material | Example 11 | Comparative Example 2 | Comparative Example 3 |
|---|---|---|---|
| (1) Beeswax | 7.0 | 7.0 | 7.0 |
| (2) Carnauba wax | 4.0 | 4.0 | 4.0 |
| (3) Squalane | 1.5 | 1.5 | 1.5 |
| (4) Stearic acid monoglyceride | 1.5 | 1.5 | 1.5 |
| (5) Stearic acid | 1.0 | 1.0 | 1.0 |
| (6) Lanolin | 2.5 | 2.5 | 2.5 |
| (7) Serecin | 2.0 | 2.0 | 2.0 |
| (8) Black iron oxide | 9.0 | 9.0 | 9.0 |
| (9) Purified water | 6.0 | 6.0 | 6.0 |
| (10) 1, 3-butylene glycol | 2.0 | 2.0 | 2.0 |
| (11) 2% hydroxyethylcellulose aqueous solution | 6.0 | 6.0 | 6.0 |
| (12) Purified water | 21.9 | 21.9 | 21.9 |
| (13) Polyethylene glycol 20000 | 5.0 | 5.0 | 5.0 |
| (14) Potassium hydroxide | 0.2 | 0.2 | 0.2 |
| (15) Paraoxybenzoate ester | 0.4 | 0.4 | 0.4 |
| (16) FA/BA (= 6/4 wt.) copolymer emulsion (30% by weight) (Preparative Example 6) | 30.0 | — | — |
| (17) FA/EMA (= 8/2 wt.) copolymer emulsion (30% by weight) (Comparative Preparative Example) | — | 30.0 | — |
| (18) FA/StA (= 6/4 wt.) copolymer emulsion (30% by weight) (Comparative Preparative Example) | — | — | 30.0 |
| Durability | ⊚ | xx | Δ |
| Water resistance | ⊚ | xx | ○ |
| Feeling when used | ○ | ○ | Δ |

The numerals in the table indicate weight percent.

EXAMPLE 12 AND COMPARATIVE EXAMPLE 4

Sun-screening lotions were prepared according to the formulations shown in Table 7. The fluorine-treated zinc oxide as a ingredient (5) indicate zinc oxide treated with 7% perfluoroalkylethyl phosphate ester diethanol amine salt. Ingredients (1) to (4) were mixed together at room temperature into a solution and were added with the ingredient (5). The mixture was dispersed by a dispersing mixer. The mixture was then emulsified by a homogenizing mixer while ingredients (6) to (11) were being added with stirring. In this way, emulsification was carried out and a sun-screening lotion was obtained. The water resistance, feeling when used, and stability of the sun-screening lotions were assessed. The results are shown in Table 7.

TABLE 7

Sun-screening lotions

| Name of raw material | Example 12 | Comparative Example 4 |
|---|---|---|
| (1) Cyclic silicone pentamer | 35 | 35 |
| (2) Perfluoropolyether | 5 | 5 |
| (3) Solution of FA/Si-MM copolymer in HFE (20% by weight) (Preparative Example 3) | 10.0 | — |
| (4) Solution of Si-MM/MMA/BMA (3/5/2 wt.) copolymer in silicone pentamer (20% by weight) (Comparative Preparative Example 1) | — | 10.0 |
| (5) Fluorine-treated zinc oxide | 5 | 5 |
| (6) Dimethylpolysiloxane/polyoxyalkylene copolymer | 3 | 3 |
| (7) Glycerin | 2 | 2 |
| (8) Ethanol | 5 | 5 |
| (9) Water | 32.9 | 32.9 |
| (10) Octyl methoxycinnamate | 2 | 2 |
| (11) Perfume | 0.1 | 0.1 |
| Durability | ⊚ | Δ |
| Water resistance | ⊚ | ⊚ |
| Feeling when used | ⊚ | x |

The numerals in the table indicate weight percent.

EXAMPLES 13 AND COMPARATIVE EXAMPLE 5

Hair rinse was prepared according to the formulations shown in Table 8. In the preparation, ingredients (1) to (8) were mixed together and heated to 80° C. and added to ingredients (9) to (11) which had been mixed at 80° C. The mixture was uniformly emulsified by a homogenizing mixer. The mixture was then cooled to room temperature. In this way, hair rinse was obtained. The hairdressing power and feeling when used of the hair rinse were assessed. The results are shown in Table 8.

TABLE 8

Hair rinse

| Name of raw material | Example 13 | Comparative Example 5 |
|---|---|---|
| (1) Stearyltrimethylammonium chloride | 3 | 3 |
| (2) Paraoxybenzoate ester | 0.3 | 0.3 |
| (3) Glycerin | 5 | 5 |
| (4) 1% No. 4 yellow aqueous solution | 0.1 | 0.1 |
| (5) 1% No. 201 green aqueous solution | 0.2 | 0.2 |
| (6) Perfume | 0.5 | 0.5 |
| (7) Polyoxyethylene (10) sorbitan monooleate | 2 | 2 |
| (8) Purified water, balance | residual portion | residual portion |
| (9) Cetyl alcohol | 2 | 2 |
| (10) Solution of FA/SMA-MM (= 2/8 wt.) copolymer in isoparaffin (20% by weight) (Preparative Example 7) | 10 | — |
| 11) Solution of FA/SMA (= 2/8 wt.) copolymer in isoparaffin (20% by weight) (Comparative Preparative Example 4) | — | 10 |
| Hairdressing power | ⊚ | Δ |
| Feeling when used | ⊚ | ⊚ |

The numerals in the table indicate weight percent.

EXAMPLE 14 AND COMPARATIVE EXAMPLE 6

Nail colors were prepared according to the formulations shown in Table 9. Ingredients (1) to (10) were mixed together by a dispersing mixer and were added with ingredients (11) and (12). The mixture was further dispersed in the dispersing mixer. In this way, a nail color was obtained. The ingredient (11) as powder was obtained by carrying out the surface treatment with the FA/Si-MM/BA (=5/2.5/2.5 wt.) copolymer of Preparative Example 8 in the same manner as in Example 4. The dispersibility of the nail colors was assessed. The results are shown in Table 9.

TABLE 9

Nail colors

| Name of raw material | Example 14 | Comparative Example 6 |
|---|---|---|
| (1) Nitrocellulose | 9 | 9 |
| (2) Alkyd resin | 9 | 9 |
| (3) Acetyltributyl citrate | 3 | 3 |
| (4) dl-camphor | 0.5 | 0.5 |
| (5) Organic bentonite | 1.5 | 1.5 |
| (6) Isopropyl alcohol | 5 | 5 |
| (7) Ethyl acetate | 10 | 10 |
| (8) Butyl acetate | 25 | 25 |
| (9) Butanol | 4 | 4 |
| (10) Toluene | 31 | 31 |
| (11) Fluorine-treated micaceous titanium which was surface-treated with an FA/Si-MM/BA (5/2.5/2.5 wt.) copolymer | 2 | — |
| (12) Fluorine-treated micaceous titanium | — | 2 |
| Dispersibility | ⊚ | x |

The numerals in the table indicate weight percent.

EXAMPLE 15

A lipstick was prepared according to the formulation shown in Table 10. In the preparation, ingredients (1) to (5) were mixed under heating and thereafter were added with ingredients (6) to (9). The mixture was passed though a three-roller mil so as to uniformly disperse the ingredients. The mixture which passed through the three-roller mill was charged in to a container and cooled. In this way, a lipstick in a pasty state was obtained. The blend composed of the FA/Si-MM (=5/5 wt.) copolymer of Preparative Example 1 (ingredient (1)) and the FA/Si-MM/BA (=5/2.5/2.5 wt.) copolymer of Preparative Example 8 (ingredient (2)) was a pasty substance imparting a novel feeling when used entirely different from that of a conventional polymer. Consequently, the lipstick comprising the blend could be spread sufficiently and uniformly and provided a particularly pleasant feeling with reduced stickiness. The oil resistance of the film, formed by the application of the lipstick, was also good.

TABLE 10

Lipstick

| Name of raw material | Example 15 |
|---|---|
| (1) FA/Si-MM (= 5/5 wt.) copolymer (Preparative Example 1) | 5 |
| (2) FA/Si-MM/BA (5/2.5/2.5 wt.) copolymer (Preparative Example 8) | 5 |
| (3) Perfluoropolyether | 2 |
| (4) Chandelier wax | 10 |
| (5) Dimethylpolysiloxane (100cS) | 54 |
| (6) Isoparaffin | 10 |
| (7) Micaceous titanium | 12 |
| (8) Organic pigment | 1 |
| (9) Inorganic pigment | 1 |

The numerals in the table indicate weight percent.

EXAMPLE 16 AND COMPARATIVE EXAMPLE 7

Zinc oxide and fine particle titanium oxide, which were treated with 2% methylhydrogenpolysiloxane, were surface-treated with the FA/Si-MM (=5/5 wt.) copolymer of Preparative Example 1 in the following way. 20 g of the silicone-treated zinc oxide, 20 g of the silicone-treated titanium oxide, 10 g of a solution of FA/Si-MM (=5/5 wt.) copolymer in a cyclic silicone pentamer (20% by weight), and 100 g of toluene were mixed together in a juice mixer for 30 seconds. The mixture was placed in an aluminum vat and dried at 60° C. for 24 hours. After being dried, the mixture was crushed by a speed cutter to thereby obtain silicone-treated powder which was further surface-treated with the FA/Si-MM copolymer. Next, Sun-screening lotions were prepared according to the formulations shown in Table 11. Ingredients (1) to (5) were mixed together by a dispersing mixer at room temperature. The mixture was then emulsified by a homogenizing mixer while ingredients (6) to (11) were being added with stirring. In this way, emulsification was carried out and a sun-screening lotion was obtained. The water resistance of Example 16 was better than that of Comparative Example 7.

TABLE 11

Sun-screening lotions

| Name of raw material | Example 16 | Comparative Example 7 |
|---|---|---|
| (1) Cyclic silicone pentamer | 35 | 35 |
| (2) Perfluoropolyether | 5 | 5 |
| (3) Cyclic silicone pentamer | 10 | 10 |
| (4) Blend powder of silicone-treated zinc oxide and fine particle titanium oxide further treated with FA/Si-MM (= 5/5 wt.) copolymer (Preparative Example 1) | 5 | — |
| (5) Blend powder of silicone-treated zinc oxide and fine particle titanium oxide | — | 5 |
| (6) Dimethylpolysiloxane/polyoxyalkylene copolymer | 3 | 3 |
| (7) Glycerin | 2 | 2 |
| (8) Ethanol | 5 | 5 |
| (9) Water | 32.9 | 32.9 |
| (10) Octyl methoxy cinnamate | 2 | 2 |
| (11) Perfume | 0.1 | 0.1 |
| Water resistance | ⊙ | Δ |
| Feeling when used | ⊙ | ⊙ |

The numerals in the table indicate weight percent.

EXAMPLE 17

10 g of FA/Si-MM (=5/5 wt.) copolymer of Preparative Example 1, 100 of perfluoropolyether (Fomblin HC/04 manufactured by Augemont Corp.), and 300 g of a cyclic silicone pentamer were charged into a sample tube. The mixture was preliminarily stirred by a homogenizing mixer for one minute and thereafter emulsified by an ultrasonic homogenizer for 5 minutes. The nonaqueous emulsion thus obtained was stored at 40° C. for one month and the stability was examined. The emulsion exhibited entirely no separation of perfluoropolyether.

EXAMPLE 18

10 g of FA/Si-MM (=5/5 wt.) copolymer of Preparative Example 1, a blend of a fluorine-containing oil A:

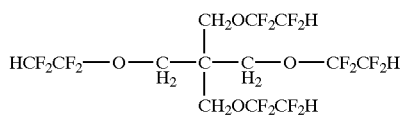

and a fluorine-containing oil B:

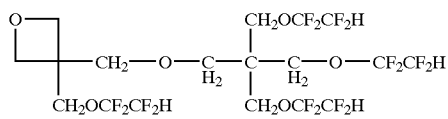

(wherein A/B=8/2 wt.), and 300 g of cyclic silicone pentamer were charged into a sample tube. The mixture was preliminarily stirred by a homogenizing mixer for one minute and thereafter emulsified by an ultrasonic homogenizer for 5 minutes. The nonaqueous emulsion thus obtained was stored at 40° C. for one month and the stability was examined. The emulsion exhibited entirely no separation of the fluorine-containing oils A and B.

Comparative Example 8

10 g of a fluorine-modified silicone [FS-1265 (100cs), manufactured by Toray Dow Corning Co., Ltd.], 100 of perfluoropolyether (Fomblin HC/04), and 300 g of cyclic silicone pentamer were charged into a sample tube. The mixture was preliminarily stirred by a homogenizing mixer for one minute and thereafter subjected to emulsification treatment by an ultrasonic homogenizer for 5 minutes. This system was not emulsified at all.

EXAMPLES 19 AND COMPARATIVE EXAMPLE 9

Creams were prepared according to the formulations shown in Table 12. In the preparation, ingredients (1) to (10) were melted under heating and thereafter were added with ingredients (11) to (14) which were also melted under heating. The mixture was uniformly emulsified and was then cooled to room temperature. In this way, creams were obtained. The cream of Example 19 provided a feeling (better spreadability and consistency) which was different from that of the cream of Comparative Example 9. Further, the water resistance of the cream of Example 19 was better than that of the cream of Comparative Example 9.

TABLE 12

Cream

| Name of raw material | Example 19 | Comparative Example 9 |
|---|---|---|
| (1) Sodium N-stearoyl-L-glutaminate | 0.4 | 0.4 |
| (2) Cetyl alcohol | 3 | 3 |
| (3) Vaseline | 3 | 3 |
| (4) Stearic acid monoglyceride | 3 | 3 |
| (5) Lanolin | 3 | 3 |
| (6) Nonaqueous emulsion of Example 18 | 10 | — |
| (7) Cyclic silicone pentamer | — | 10 |
| (8) Sorbitan sesquioleate | 0.5 | 0.5 |
| (9) Polyoxyethylene/polyoxypropylene block copolymer (Pluronic F-68) | 3 | 3 |
| (10) Perfume | 0.1 | 0.1 |
| (11) 1, 3-butylene glycol | 8 | 8 |
| (12) Antiseptic | 0.1 | 0.1 |
| (13) Glycerin | 10 | 10 |
| (14) Purified water | 55.9 | 55.9 |

The numerals in the table indicate weight percent.

EXAMPLE 20

10 g of FA/SMA-MM (=2/8 wt.) copolymer of Preparative Example 7, 100 g of perfluoropolyether (Fomblin HC/04), and 300 g of fluid paraffin were charged into a sample tube and uniformly melted by heating at 80° C. The mixture was preliminarily stirred by a homogenizing mixer for one minute and thereafter emulsified by an ultrasonic homogenizer for 5 minutes. The nonaqueous emulsion thus obtained was stored at 40° C. for one month and the stability was observed. The emulsion exhibited entirely no separation of perfluoropolyether.

EXAMPLES 21 AND 22

Comparative Example 10

An FA/Si-MM/DAAAM/methacrylic acid (5/3.75/1/0.25 wt.) copolymer was obtained (Example 21) by carrying out polymerization and separation in the same manner as in Example 1, except that 20 g of Si-MM as a monomer was replaced by 15 g of Si-MM, 4 g of diacetone acrylamide and 1 g of methacrylic acid. Further, an FA/Si-MM/urethane monomer (5/3.75/1.25 wt.) copolymer was obtained (Example 22) by carrying out polymerization and separation in the same manner as in Example 1, except that 20 g of Si-MM as a monomer was replaced by 15 g of Si-MM and 5 g of a urethane monomer having the following formula.

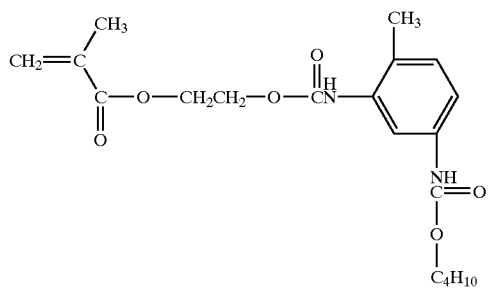

By using these polymers, set lotions were prepared according to the formulations shown in Table 13. In the preparation, ingredients (4) to (9) were first dissolved to form a solution and the resulting solution was added with ingredients (1) to (3) to cause wetting and dissolution. Then, ingredient (9) was gradually added with stirring.

TABLE 13

Set lotions

| Name of raw material | Example 21 | Example 22 | Comparative Example 10 |
| --- | --- | --- | --- |
| (1) FA-Si-MM/DAAAM/methacrylic acid (5/3.75/1/0.25 wt.) copolymer | 3 | — | — |
| (2) FA/Si-MM/urethane monomer (5/3.75/1.25 wt.) copolymer | — | 3 | — |
| (3) Polyvinylpyrrolidone | — | — | 3 |
| (4) Polyoxyethylene(20) oleyl ether | 5 | 5 | 5 |
| (5) 1, 3-butylene glycol | 10 | 10 | 10 |
| (6) Ethanol | 5 | 5 | 5 |
| (7) Paraoxybenzoate ester | 0.1 | 0.1 | 0.5 |
| (8) Dye | trace amount | trace amount | trace amount |
| (9) Perfume | 0.5 | 0.5 | 0.5 |
| (10) Purified water, to make up to 100 | to be 100 | to be 100 | to be 100 |
| Hairdressing power after hair washing | ⊚ | ⊚ | ⊚ |
| Feeling after hair washing | ⊚ | ⊚ | Δ |

The numerals in the table indicate weight percent.

EXAMPLE 23 AND COMPARATIVE EXAMPLE 11

Powdery foundations were prepared according to the formulations shown in Table 14 using FA/Si-MM (=5/5 wt.) copolymer of Preparative Example 1. In the preparation, ingredients (1) and (2) were mixed and crushed in an atomizer. The blend was then placed in a Henschel mixer and were added with ingredients (3) to (6) which had been melted. The ingredients in the mixer were uniformly mixed. The blend was then placed in a mold and press-molded to thereby form a powdery foundation.

TABLE 14

Powdery foundation

| Name of raw material | Example 23 | Comparative Example 11 |
| --- | --- | --- |
| (1) Blend powder | 89.8 | 89.8 |
| (2) Paraoxybenzoate ester | 0.1 | 0.1 |
| (3) FA/Si-MM (= 5/5 wt.) copolymer | 8.0 | — |
| (4) Vaseline | — | 8.0 |
| (5) Dimethylpolysiloxane | 2.0 | 2.0 |
| (6) Perfume | 0.1 | 0.1 |
| Durability | ⊚ | Δ |
| Water resistance | ⊚ | Δ |
| Feeling when used | ⊚ | ○ |

The numerals in the table indicate weight percent.

EXAMPLE 24 AND COMPARATIVE EXAMPLE 12

The copolymer obtained in Preparative Example 1 or 8 was dissolved in cyclic silicone pentamer or isoparaffin (Isopar G, manufactured by Exxon Corp.) to give a solution having a concentration of 5% by weight. Then, the interfacial tension between the solution and perfluoropolyether (Demnum S-20, manufactured by Daikin Industries, Ltd.) was measured in accordance with a spinning drop method [using an interfacial tensiometer, according to a spinning drop method, SITE-04 manufactured by Kurz Corp. (Germany)]. On the other hand, for the purpose of comparison, a fluorine-free acrylic/silicone copolymer [KP-545 (a polymer composed of Si-MM/methyl methacrylate/butyl methacrylate/2-ethylhexyl acrylate=50/35/7.5/7.5 wt.), manufactured by Shin-Etsu Chemical Co., Ltd.] and a fluorine-modified silicone FS-1265 were also subjected the same measurement. The results are shown in Table 15. The incorporation of the copolymer of the present invention into the fluorine-free solvent caused the interfacial tension to drop by 20 to 70% relative to the case when the copolymer was not incorporated. This is the evidence that the copolymer is adsorbed on the perfluoropolyether/fluorine-free solvent interface. In the case of the comparative example, the drop in the interfacial tension is not observed at all and therefore it is understood that the fluorine-free, acrylic/silicone copolymer or the fluorine-modified silicone is merely dissolved in the fluorine-free solvent and therefore cannot be adsorbed to the interface.

EXAMPLE 25 AND COMPARATIVE EXAMPLE 13

10 g of the perfluoropolyether used in Example 24 and Comparative Example 12 and 20 g of the 5% by weight solution of the copolymer in cyclic silicone pentamer or 20 g of the 5% by weight solution of the copolymer in isoparaffin were emulsified for one minute in an ultrasonic homogenizer. Whereas the copolymer of the present invention capable of causing the decrease in the interfacial tension produced a stable emulsion comprising fine particles having a particle size of about 200 to 300 nm, the comparative example did not produce any emulsion at all.

TABLE 15

Interfacial tension of perfluoropolyether/fluorine-free solvent interface (mN/m)
(concentration of the copolymer: 5% by weight in a fluorine-free solvent)

| | Preparative Example | Ingredients of Polymer | Cylcic silicone pentamer | Ratio of interfacial tension (%) | Isoparaffin | Ratio of interfacial tension (%) |
|---|---|---|---|---|---|---|
| Silicon-containing compound | — | When no copolymer is incorporated | 5.43 | — | 5.58 | — |
| Si—MA | 1 | FA/Si—MM = 5/5 wt. | 3.84 | 71 | 3.41 | 61 |
| | 8 | FA/Si—MM/BA = 5/2.5/2.5 wt. | 1.77 | 33 | 1.46 | 26 |
| Comparative Example | Acrylic/silicone copolymer | Si—MM/MMA/BMA/2EHA = 50/35/7.5/7.5 wt. | 5.44 | 100 | 5.49 | 98 |
| | Fluorine-modified silicone | FS-1265 (substituent group: —CH$_2$CH$_2$CF$_3$) | 5.44 | 100 | 5.62 | 101 |

EFFECTS OF THE INVENTION

The copolymer for cosmetics of the present invention can be easily incorporated in conventional cosmetics. When applied on the skin, the cosmetic incorporated with copolymer of the present invention forms a film excellent in water resistance, water- and oil-repellency, feeling when used, and safety.

Further, the copolymer for cosmetics acts as a compatibilizer between a fluorine-containing material and a fluorine-free material, thereby stabilizing the cosmetics. Furthermore, when powder treated with a fluorine-containing compound is further surface-treated with the copolymer for cosmetics, the following drawbacks of the powder treated with a fluorine-containing compound can be alleviated.

poor affinity for a fluorine-free material,
unsatisfied feeling such as inferior spreadability and adhesion when used,
dust formation when the cosmetics are prepared, and
poor dispersibility in a fluorine-free solvent.

What is claimed is:

1. A cosmetic comprising a raw material for a cosmetic and a copolymer, said copolymer comprising
   (A) 5 to 95% by weight of repeating units derived from a fluorine-containing (meth)acrylate, and
   (B) 95 to 5% by weight of repeating units derived from at least one fluorine-free monomer selected from the group consisting of a silicone macromonomer, a polyalkylene glycol (meth)acrylate, an alkyl (meth)acrylate macromonomer, and an alkyl (meth)acrylate,
   wherein the copolymer comprises:
   (i) a fluorine-containing (meth)acrylate and a silicone macromonomer,
   (ii) a fluorine-containing (meth)acrylate and a polyalkylene glycol (meth)acrylate,
   (iii) a fluorine-containing (meth)acrylate and an alkyl (meth)acrylate macromonomer,
   (iv) a fluorine-containing (meth)acrylate and a $C_{1-4}$ alkyl-containing alkyl (meth)acrylate,
   (v) a fluorine-containing (meth)acrylate, a silicone macromonomer, and a $C_{1-4}$ alkyl-containing alkyl (meth)acrylate, or
   (vi) a fluorine-containing (meth)acrylate, a silicone macromonomer, and an alkyl (meth)acrylate macromonomer;

wherein the copolymer is dissolved or dispersed in a medium, and the medium is a hydrofluoroether represented by the general formula:

wherein n is a number of 1 to 12, m is a number of 0 to 25, l is a number of 0 to 11, m+l is equal to 2n+1, x is a number of 1 to 12, y is a number of 0 to 25, z is a number of 0 to 11, and y+z is equal to 2x+1, with the proviso that m and y are not simultaneously 0 and that l and z are not simultaneously 0.

2. The cosmetic of claim 1, wherein the fluorine-containing (meth)acrylate is a compound represented by the following formula (I-1):

$$\begin{array}{c} X \\ | \\ CH_2{=}C \\ | \\ COO{-}A{-}Rf \end{array} \quad (I\text{-}1)$$

wherein Rf is a polyfluoroalkyl group having 6 to 16 carbon atoms or a perfluoropolyether group; and A is an alkylene group having 1 to 4 carbon atoms,

wherein $R^1$ is an alkyl group having 1 to 4 carbon atoms and $R^2$ is an alkylene group having 1 to 4 carbon atoms, or

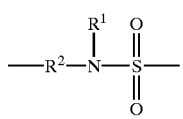

; and

X is a hydrogen atom or a methyl group; or
a fluorine-containing (meth)acrylate macromonomer represented by the following formula (I-2):

(1-2)

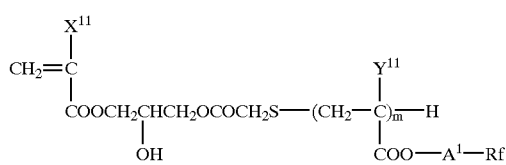

wherein Rf is a polyfluoroalkyl group having 6 to 16 carbon atoms or a perfluoropolyether group; $A^1$ is an alkylene group having 1 to 4 carbon atoms,

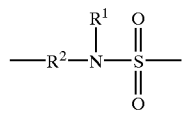

wherein $R^1$ is an alkyl group having 1 to 4 carbon atoms and $R^2$ is an alkylene group having 1 to 4 carbon atoms, or

$X^{11}$ is a hydrogen atom or a methyl group; $Y^{11}$ is a hydrogen atom or a methyl group; and m is 5 to 100.

3. The cosmetic of claim 1, wherein the silicon macromonomer is represented by the following formula (II-1):

(II-1)

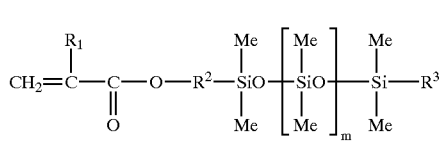

wherein Me is a methyl group and $R^1$ is a methyl group or a hydrogen atom; $R^2$ is a divalent saturated hydrocarbon group having 1 to 10 carbon atoms which has a straight or branched carbon chain and which may be disjoined by one or two ether linkages in some cases; $R^3$ is an alkyl group having 2 to 4 carbon atoms; and m is 3 to 300.

4. The cosmetic of claim 1, wherein the polyalkylene glycol (meth)acrylate is represented by the following formula (II-2):

(II-2)

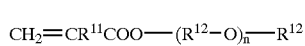

wherein $R^{11}$ and $R^{13}$ are each a hydrogen atom or a hydrogen atom or a methyl group; R12 is an alkylene group having 2 to 6 carbon atoms; and n is an integer of 1 to 50.

5. The cosmetic of claim 1, wherein the alkyl (meth) acrylate macromonomer is represented by the following formula (II-3):

(II-3)

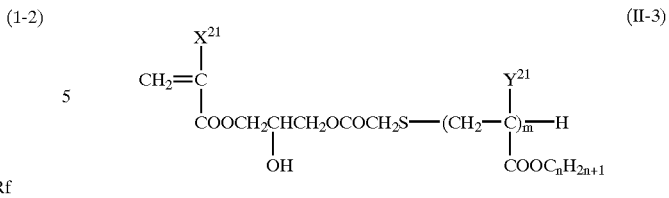

wherein $X^{21}$ and $Y^{21}$ are each a hydrogen atom or a methyl group; n is 1 to 22; and m is 5 to 100.

6. The cosmetic of claim 1, wherein the $C_{1-4}$ alkyl-containing alkyl (meth)acrylate is represented by the following formula (II-4):

(II-4)

wherein X is a hydrogen atom or a methyl group; and n is 1 to 4 for the $C_{1-4}$ alkyl-containing alkyl (meth)acrylate.

7. The cosmetic of claim 1, wherein 1 to 50% by weight of the copolymer is dissolved or dispersed in a medium.

8. A method of using a composition as a cosmetic, comprising:

providing the composition; and applying the composition as a cosmetic to a person, wherein the composition comprises 0.1 to 30% by weight of a copolymer and at least 0.1% by weight of a fluorine-containing compound-treated powder, a fluorine-containing oil, or a mixture of a fluorine-containing compound-treated powder and a fluorine-containing oil, wherein the copolymer comprises:
(A) 5 to 95% by weight of repeating units derived from a fluorine-containing (meth)acrylate, and
(B) 95 to 5% by weight of repeating units derived from at least one fluorine-free monomer selected from the group consisting of a silicone macromonomer, a polyalkylene glycol (meth)acrylate, an alkyl (meth)acrylate macromonomer, and an alkyl (meth)acrylate, and wherein the copolymer comprises:
(i) a fluorine-containing (meth)acrylate and a silicone macromonomer,
(ii) a fluorine-containing (meth)acrylate, a silicone macromonomer, and a $C_{1-4}$ alkyl-containing alkyl (meth)acrylate, or
(iii) a fluorine-containing (meth)acrylate, a silicone macromonomer, and an alkyl (meth)acrylate macromonomer.

9. A method of using a composition as a cosmetic, comprising:

providing the composition; and applying the composition as a cosmetic to a person, wherein the composition comprises a copolymer, a powder treated with a fluorine-containing compound and/or a fluorine-containing oil, and a fluorine-free compound, wherein the copolymer acts as a compatibilizer or a dispersant so that the powder treated with a fluorine-containing compound and/or the fluorine-containing oil is compatibilized with or dispersed in the fluorine-free compound, wherein the copolymer comprises:
(A) 5 to 95% by weight of repeating units derived from a fluorine-containing (meth)acrylate, and
(B) 95 to 5% by weight of repeating units derived from at least one fluorine-free monomer selected from the group consisting of a silicone macromonomer, a polyalkylene glycol (meth)acrylate, an alkyl (meth)acrylate macromonomer, and an alkyl (meth)acrylate,
wherein the copolymer comprises:
(i) a fluorine-containing (meth)acrylate and a silicone macromonomer,
(ii) a fluorine-containing (meth)acrylate, a silicone macromonomer, and a $C_{1-4}$ alkyl-containing alkyl (meth)acrylate, or
(iii) a fluorine-containing (meth)acrylate, a silicone macromonomer, and an alkyl (meth)acrylate macromonomer.

10. A cosmetic comprising powder treated with a fluorine-containing compound which is further surface-treated with a copolymer, wherein the copolymer comprises:
(A) 5 to 95% by weight of repeating units derived from a fluorine-containing (meth)acrylate, and
(B) 95 to 5% by weight of repeating units derived from at least one fluorine-free monomer selected from the group consisting of a silicone macromonomer, a polyalkylene glycol (meth)acrylate, an alkyl (meth)acrylate macromonomer, and an alkyl (meth)acrylate, wherein the copolymer comprises:
(i) a fluorine-containing (meth)acrylate and a polyalkylene glycol (meth)acrylate,
(ii) a fluorine-containing (meth)acrylate and an alkyl (meth)acrylate macromonomer,
(iii) a fluorine-containing (meth)acrylate and a $C_{1-4}$ alkyl-containing alkyl (meth)acrylate,
(iv) a fluorine-containing (meth)acrylate, a silicone macromonomer, and a $C_{1-4}$ alkyl-containing alkyl (meth)acrylate, or
(v) a fluorine-containing (meth)acrylate, a silicone macromonomer, and an alkyl (meth)acrylate macromonomer
wherein the silicone macromonomer is represented by the following formula (II-1):

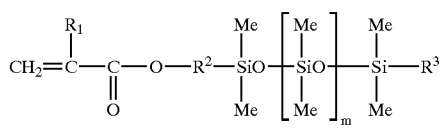

(II-1)

wherein Me is a methyl group and $R^1$ is a methyl group or a hydrogen atom; $R^2$ is a divalent saturated hydrocarbon group having 1 to 10 carbon atoms which has a straight or branched chain and which may be disjoined by one or two ether linkages in some cases; $R^3$ is an alkyl group having 2 to 4 carbon atoms; and m is 3 to 300.

11. The cosmetic of claim 10, wherein the powder, which is treated with a fluorine-containing compound, is the powder which is treated with a fluorine-containing phosphate ester having the following general formula:

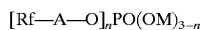

wherein Rf is a polyfluoroalkyl group having 6 to 16 carbon atoms or a perfluoropolyether group; A is an alkylene group having 1 to 4 carbon atoms,

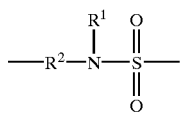

wherein $R^1$ is an alkyl group having 1 to 4 carbon atoms and $R^2$ is an alkylene group having 1 to 4 carbon atoms, or

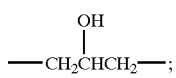

M is a hydrogen atom, a metal atom, ammonium, or substituted ammonium; and n is a number of 1 to 3.

12. The method of claim 8 or 9, wherein the fluorine-containing oil is a perfluoropolyether, a hydrofluoroether, or a compound represented by the general formula:

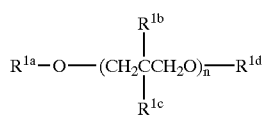

wherein $R^{1a}$ and $R^{1d}$ are each a hydrogen atom or a partially or completely fluorinated aliphatic group having 1 to 20 carbon atoms; $R^{1b}$ and $R^{1c}$ are each a hydrogen atom, or an aliphatic group having 1 to 20 carbon atoms, or a partially or completely fluorinated aliphatic group having 1 to 20 carbon atoms, with the proviso that at least one of $R^{1a}$ to $R^{1d}$ is a partially or completely fluorinated aliphatic group having 1 to 20 carbon atoms; and n is a number of 1 to 20, or
by the general formula:

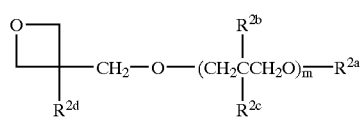

wherein $R^{2a}$ is a hydrogen atom or a partially or completely fluorinated aliphatic group having 1 to 20 carbon atoms; $R^{2b}$, $R^{2c}$ and $R^{2d}$ are each an aliphatic group having 1 to 20 carbon atoms or a partially or completely fluorinated aliphatic group having 1 to 20 carbon atoms, with the proviso that at least one of $R^{2a}$ to $R^{2d}$ is a partially or completely fluorinated aliphatic group having 1 to 20 carbon atoms; and m is a number of 1 to 20.

13. A cosmetic comprising a silicone-treated powder which is further surface-treated with a copolymer, wherein the copolymer comprises:
(A) 5 to 95% by weight of repeating units derived from a fluorine-containing (meth)acrylate, and
(B) 95 to 5% by weight of repeating units derived from at least one fluorine-free monomer selected from the group consisting of a silicone macromonomer, a polyalkylene glycol (meth)acrylate, an alkyl (meth)acrylate macromonomer, and an alkyl (meth)acrylate, wherein the copolymer comprises:
(i) a fluorine-containing (meth)acrylate and a polyalkylene glycol (meth)acrylate,
(ii) a fluorine-containing (meth)acrylate and an alkyl (meth)acrylate macromonomer,
(iii) a fluorine-containing (meth)acrylate and a $C_{1-4}$ alkyl-containing alkyl (meth)acrylate, (iv) a fluorine-containing (meth)acrylate, a silicone macromonomer, and a $C_{1-4}$alkyl-containing alkyl (meth)acrylate, or (v) a fluorine-containing (meth)acrylate, a silicone macromonomer, and an alkyl (meth)acrylate macromonomer and wherein the silicone macromonomer is represented by the following formula (II-1):

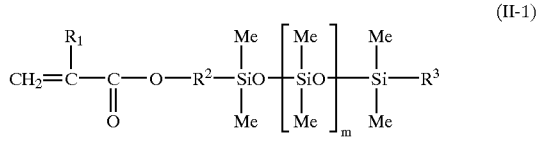

wherein Me is a methyl group and $R^1$ is a methyl group or a hydrogen atom; $R^2$ is a divalent saturated hydrocarbon group having 1 to 10 carbon atoms which has a straight or branched carbon chain and which may be disjoined by one or two ether linkages in some cases; $R^3$ is an alkyl group having 2 to 4 carbon atoms; and m is 3 to 300.

14. A method of using a composition as a cosmetic containing a nonaqueous emulsion, which is prepared by emulsifying a fluorine-containing oil in a fluorine-free solvent by using as an emulsifier a copolymer for the cosmetic, comprising:

providing the composition; and applying the composition as a cosmetic to a person, wherein:

the copolymer for the cosmetic comprises:

(1) a fluorine-containing (meth)acrylate and a silicone macromonomer, or (2) a fluorine-containing (meth)acrylate, a silicone macromonomer and an alkyl (meth)acrylate macromonomer;

wherein the fluorine-free solvent is a silicone-based solvent, a hydrocarbon-based solvent, an ester-based solvent, or a ketone-based solvent; and the fluorine-containing oil is a perfluoropolyether, a hydrofluoroether, or a compound represented by the general formula:

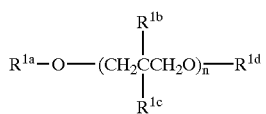

wherein $R^{1a}$ and $R^{1d}$ are each a hydrogen atom or a partially or completely fluorinated aliphatic group having 1 to 20 carbon atoms; $R^{1b}$ and $R^{1c}$ are each a hydrogen atom, or an aliphatic group having 1 to 20 carbon atoms, or a partially or completely fluorinated aliphatic group having 1 to 20 carbon atoms, with the proviso that at least one of $R^{1a}$ to $R^{1d}$ is a partially or completely fluorinated aliphatic group having 1 to 20 carbon atoms; and n is a number of 1 to 20, or by the general formula:

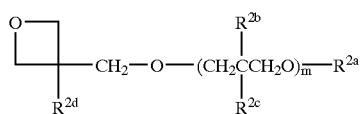

wherein $R^{2a}$ is a hydrogen atom or a partially or completely fluorinated aliphatic group having 1 to 20 carbon atoms; $R^{2b}$, $R^{2c}$ and $R^{2d}$ are each an aliphatic group having 1 to 20 carbon atoms or a partially or completely fluorinated aliphatic group having 1 to 20 carbon atoms, with the proviso that at least one of $R^{2a}$ to $R^{2d}$ is a partially or completely fluorinated aliphatic group having 1 to 20 carbon atoms; and m is a number of 1 to 20.

\* \* \* \* \*